(12) United States Patent
Leyte Guerrero et al.

(10) Patent No.: US 9,920,435 B2
(45) Date of Patent: Mar. 20, 2018

(54) METHODOLOGY FOR THREE-DIMENSIONAL MORPHOLOGICAL AND QUANTITATIVE DETERMINATION OF MICRO AND NANOCAVITIES PRODUCED BY CHEMICAL AND MICROBIOLOGICAL CORROSION IN METALLIC MATERIALS

(71) Applicant: INSTITUTO MEXICANO DEL PETRÓLEO, Mexico City (MX)

(72) Inventors: Florentino Leyte Guerrero, México, D.F. (MX); Vicente Garibay Febles, México, D.F. (MX); Ubaldo Sadott Pacheco y Alcalá, México, D.F. (MX); Norma Icoquih Zapata Peñasco, México, D.F. (MX); Gustavo Roberto Pérez Lemus, México, D.F. (MX); Marco Antonio Valadez Martínez, México, D.F. (MX)

(73) Assignee: INSTITUTO MEXICANO DEL PETROLEO, Mexico City (MX)

( * ) Notice: Subject to any disclaimer, the term of this patent is extended or adjusted under 35 U.S.C. 154(b) by 0 days.

(21) Appl. No.: 14/964,431

(22) Filed: Dec. 9, 2015

(65) Prior Publication Data
US 2016/0245738 A1 Aug. 25, 2016

(30) Foreign Application Priority Data
Dec. 17, 2014 (MX) .................... MX/a/2014/015591

(51) Int. Cl.
C23F 11/04 (2006.01)
C25F 3/14 (2006.01)
G01N 17/04 (2006.01)

(52) U.S. Cl.
CPC ............. *C23F 11/04* (2013.01); *C25F 3/14* (2013.01); *G01N 17/043* (2013.01); *G01N 2223/079* (2013.01); *G01N 2223/418* (2013.01)

(58) Field of Classification Search
USPC ......................................................... 250/310
See application file for complete search history.

(56) References Cited

U.S. PATENT DOCUMENTS

| | | | | |
|---|---|---|---|---|
| 3,992,198 A | * | 11/1976 | Demo, Jr. ................ | C22C 38/28 420/62 |
| 7,754,342 B2 | * | 7/2010 | Hazel ....................... | C23C 4/04 416/241 B |
| 2010/0261029 A1 | * | 10/2010 | Borysenko ............ | C09C 1/0081 428/562 |
| 2012/0317956 A1 | * | 12/2012 | Di Salvo ................... | F02K 9/52 60/204 |

OTHER PUBLICATIONS

"Corrosion in the oil industry", Oilfield review, Shlumberger V6(2) Apr. 1994, Brondel, E. et al, pp. 4-69.

ASTM G1-90 (2003) "Standard Practice for Preparing, Cleaning, and EvaluatingCorrosion Test Specimens".
Chawla, N., Williams, J.J., Deng, X., McClimon, C., 2009 "ThreeDimensional (30) Characterization and Modeling of Porosity in PowderMetallurgy (P/M) Steels." International Journal of Powder Metallurgy, 45(2).
Pittman, E. D., Duschatko, R. W. 1970 paper: "Use of pore casts and scanning electron microscope to study pore geometry", Journal of Sedimentary Petrology. 40(4 ), 1153-1157).
Freire-Gormaly, M., Maclean, H., Bazylak, A. 2012 "Microct investigations and pore network reconstructions of limestone and carbonate-based rocks for deep geologic carbon sequestration." Proceedings of the 6th International Conference on Energy Sustainability Conference, ASME2013, Jul. 23-24, San Diego, California, USA.
Vaidya, R, U., Hill, M.A. Hawley, M., Bull, D. P. (1998) "Effect of Pitting Corrosion in NaCl Solutions on the Statistics of Fracture of Beryllium." Metallurgical and Materila Transactions A 29A. November. 2753-2760.
Fraser, H.L., Mills, M. J., Buchheit, R. G., Wang, Y., Ghosh, S., Williams, J. C., Frankel, G. S. Rollett, A D. Grandt, A F. (2008) "accelerated metalsdevelopment by Computation" Air Force Research Laboratory Materials andManufacturing Directorate Wright-Patterson Air Force Base, OH 45433-7750 Air Force Materiel Command United States Air Force. Report AFRL-RX-WP-TR-2008-4176.
Halvarsson, M., Tang, J.E., Asteman, H., Svensson, J.-E., Johansson, L.—G.2006 "Microstructural investigation of the breakdown of the protective oxide scale on a 304 steel in the presence of oxygen and water vapour at 600oC." Corrosion Science 48: 2014-2035.
"In situ electrochemical SPM for energy and corrosion studies", American Laboratory, Aug. 17, 2011.

* cited by examiner

*Primary Examiner* — Philip A Johnston
(74) *Attorney, Agent, or Firm* — Lisa V. Mueller; Michael Best & Friedrich LLP

(57) ABSTRACT

The present invention refers to a procedure which includes the following objectives:
a) To determine the morphology of the micro and nanocavities produced by chemical and/or microbiological corrosion in metallic materials, in the space of three dimensions as well as the effective advance of corrosion, the true length of corrosion cavities and their associated parameters: corrosion vectors, corrosion intensity and determination of the cavities diameter/true length of corrosion ratio, applying scanning electron microscopy (MEB) techniques, and analytic, gravimetric and volumetric formulations;
b) To quantitatively determine the rate of chemical and/or microbiological corrosion in metallic materials, through their volumetric and gravimetric properties; and
c) To obtain a graphic interface to access the numeric information and the micrographs in a simple and friendly manner.
More specifically, the present invention is related to the laboratory procedures, analytic expressions, devices, procedures and calculations required to characterize the micro and nanocavities of coupons and biocoupons, caused by chemical and/or microbiological pitting and uniform corrosion.

20 Claims, 34 Drawing Sheets

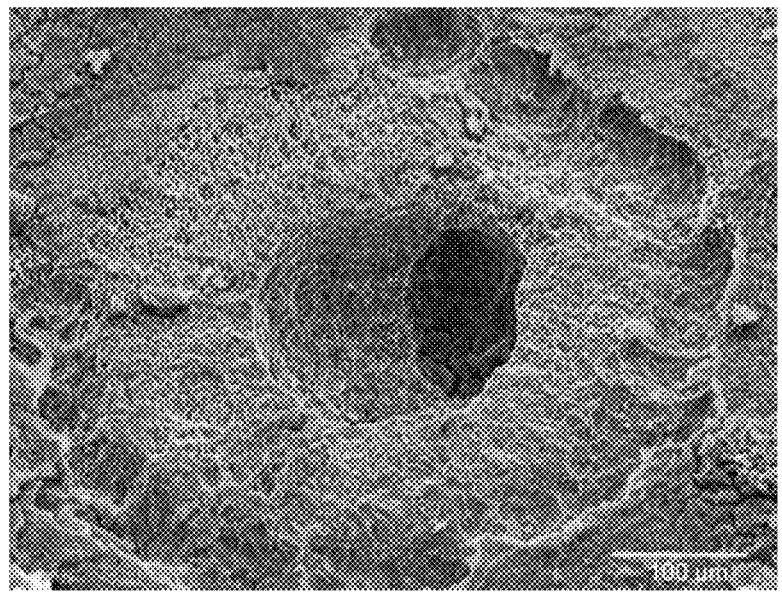
Figure No. 1
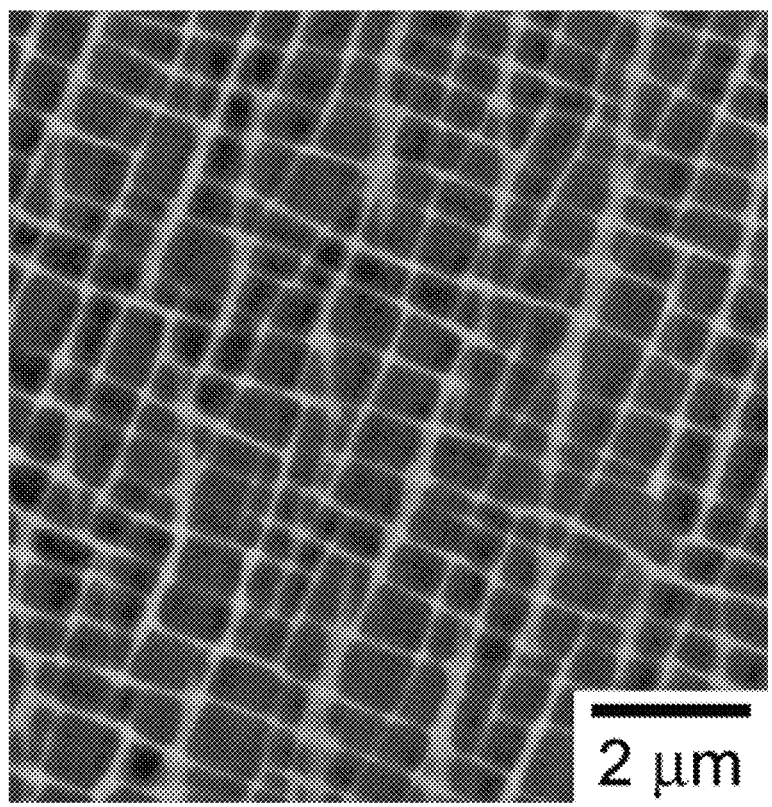
Figure No. 2

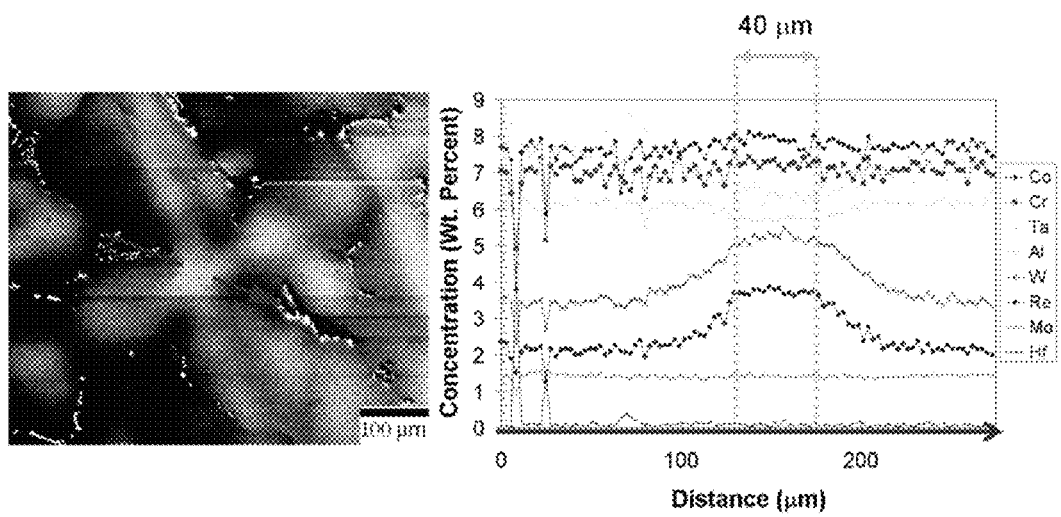
Figure No. 3
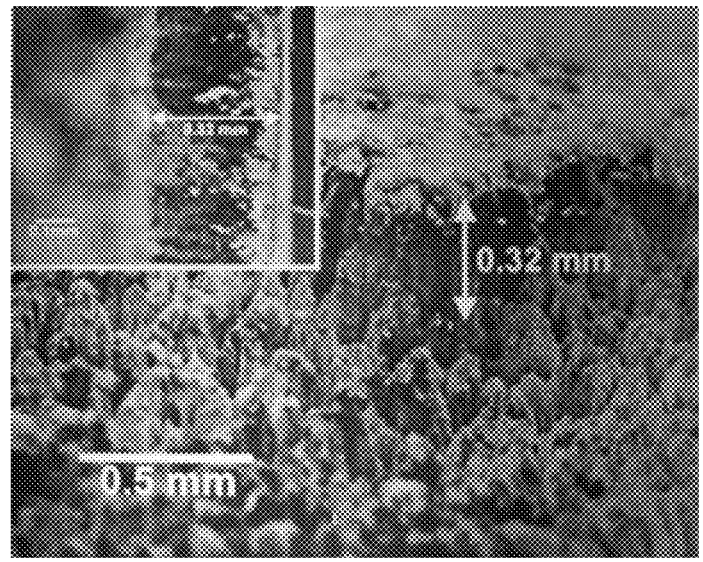
Figure No. 4

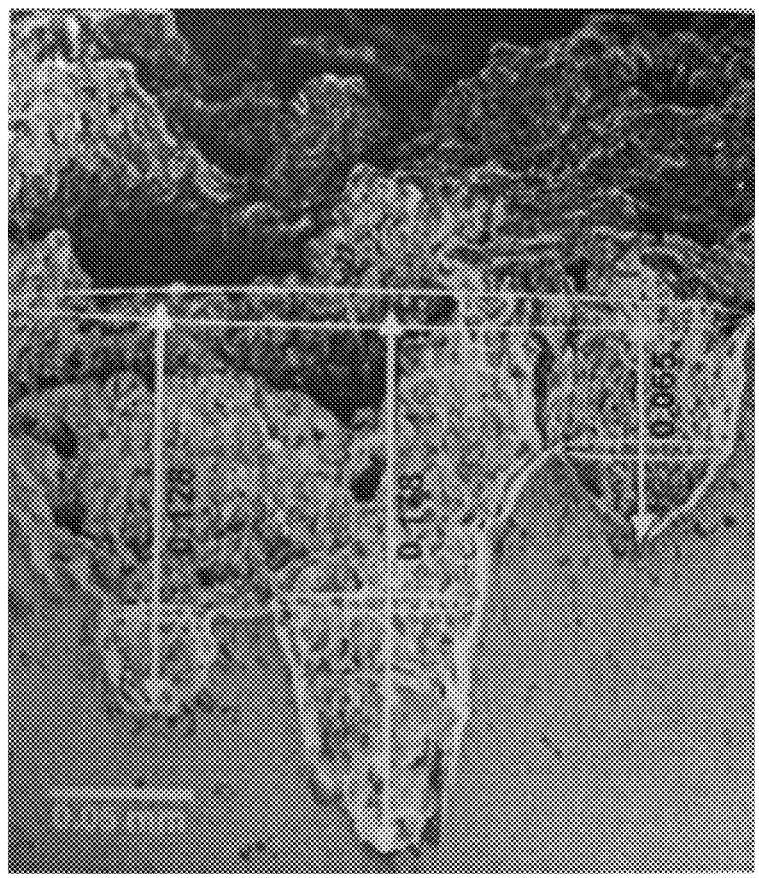
Figure No. 5
Figure No. 6

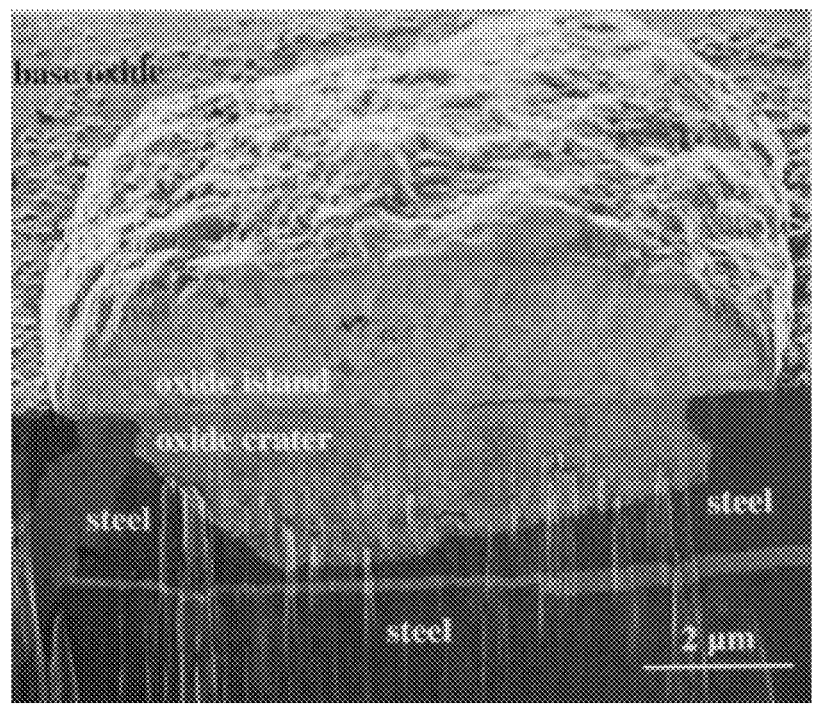
Figure No. 7
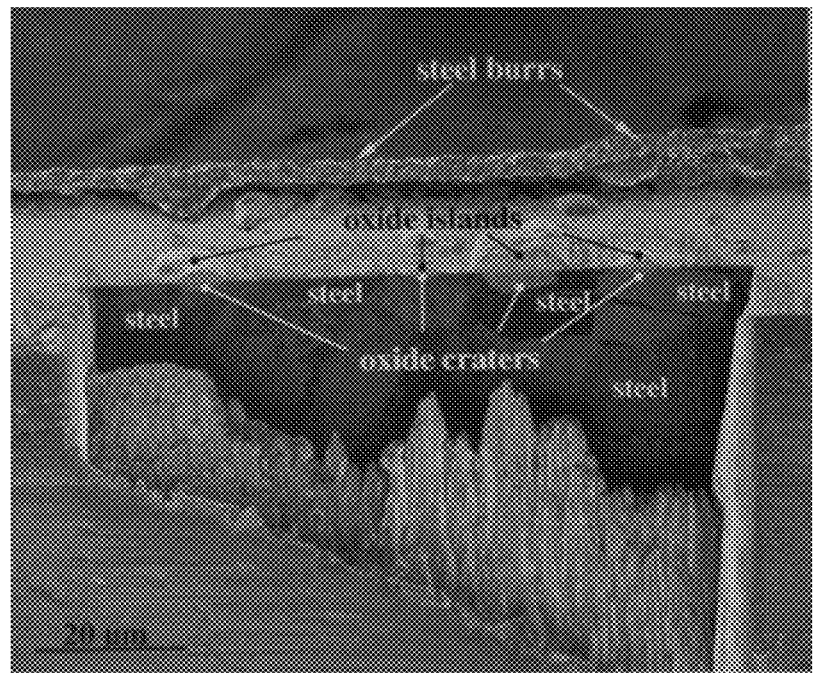
Figure No. 8

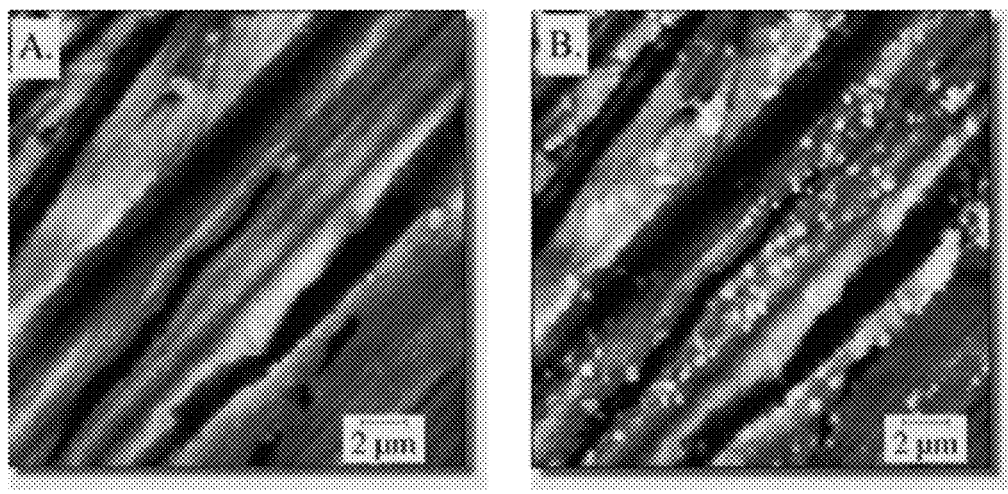
Figure No. 9
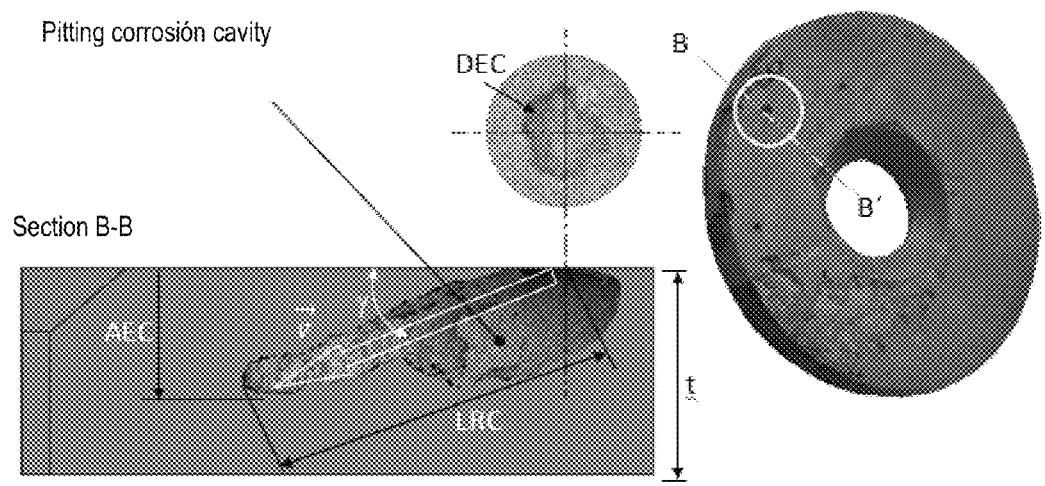
Figure No. 10

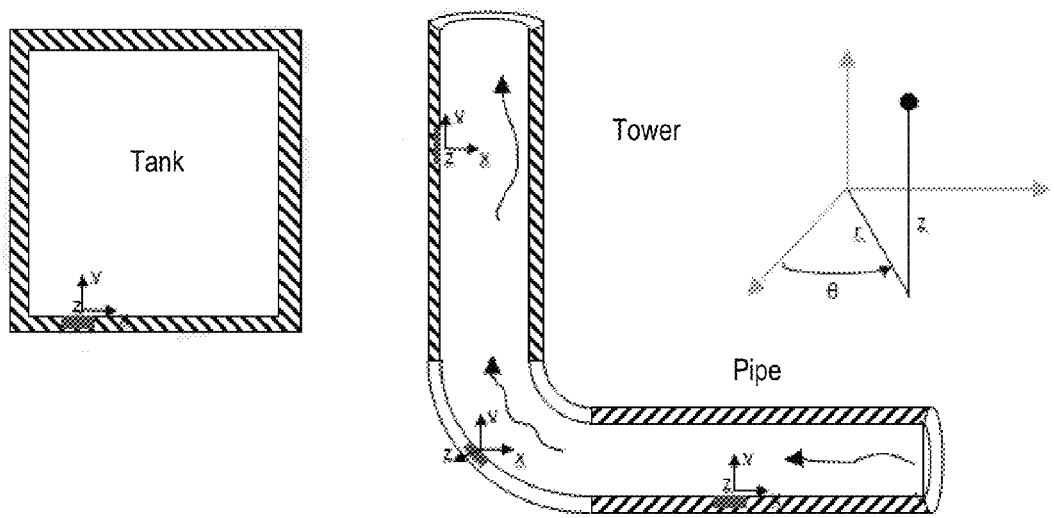
Figure No. 11
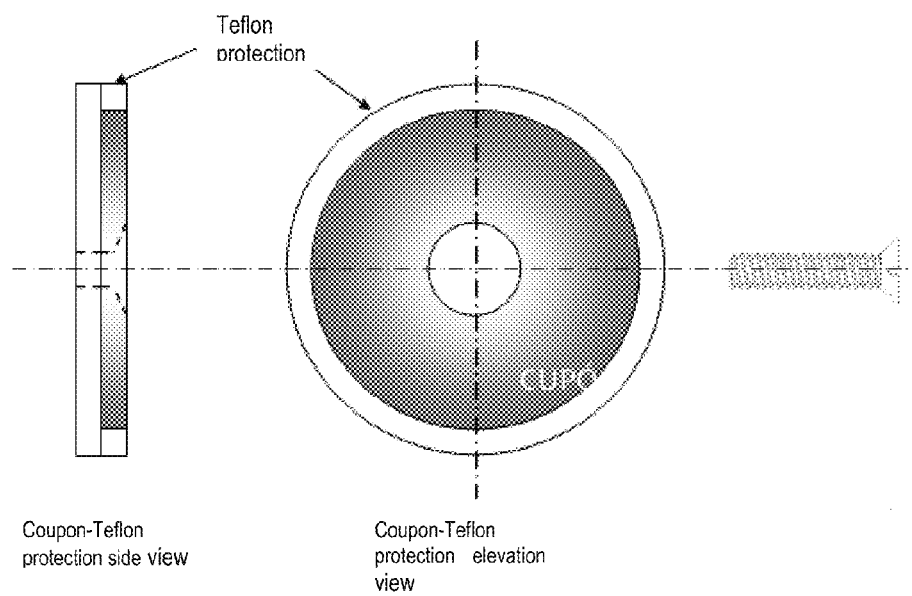
Coupon-Teflon
protection side view
Coupon-Teflon
protection elevation
view
Figure No. 12

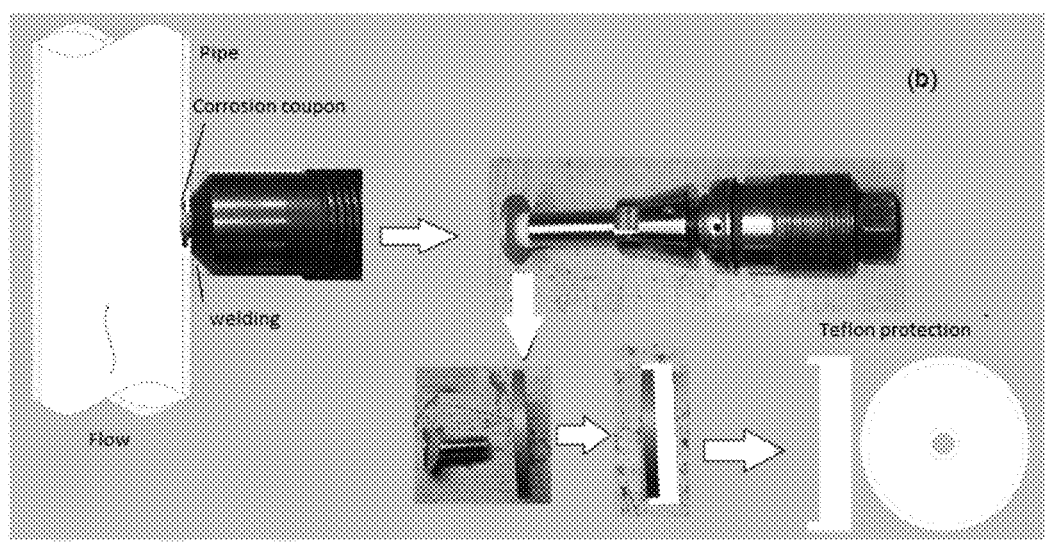
Figure No. 13

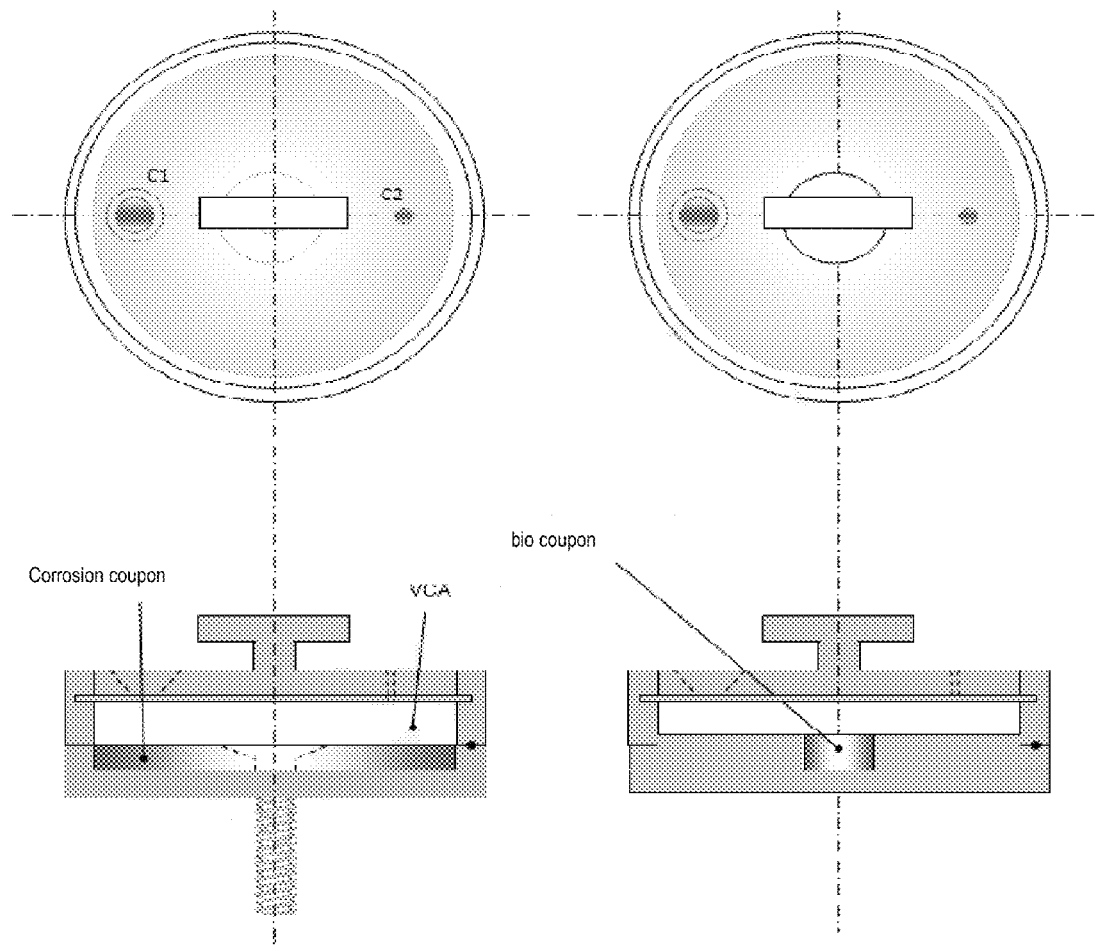
Figure No. 14　　　　Figure No. 15

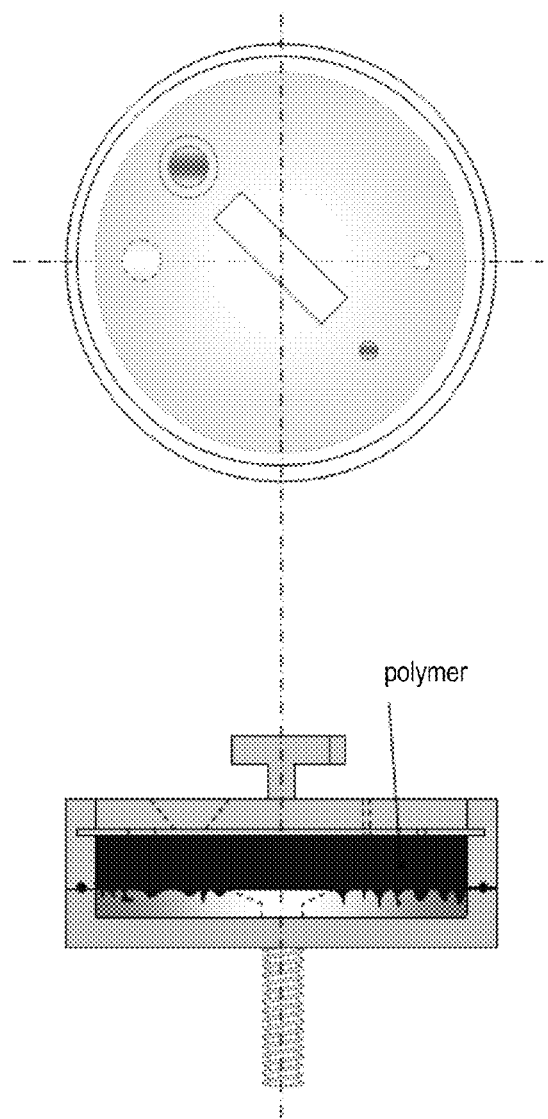
Figure No. 16
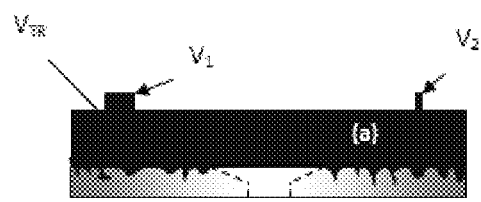
Figure No. 17
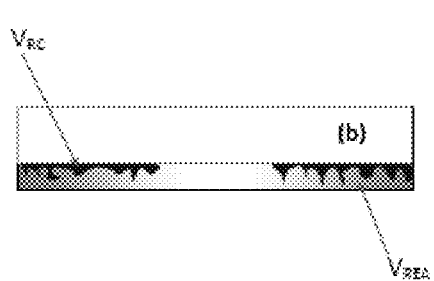
Figure No. 18

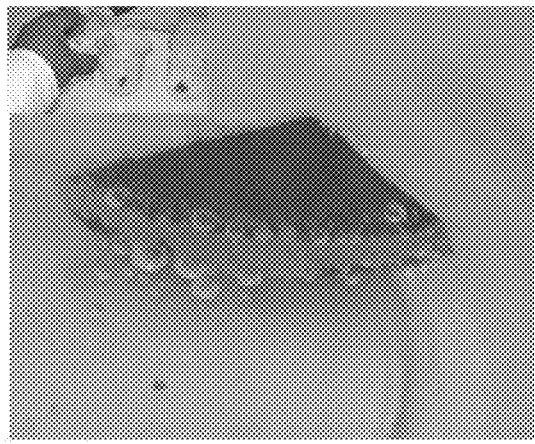
Figure No. 19
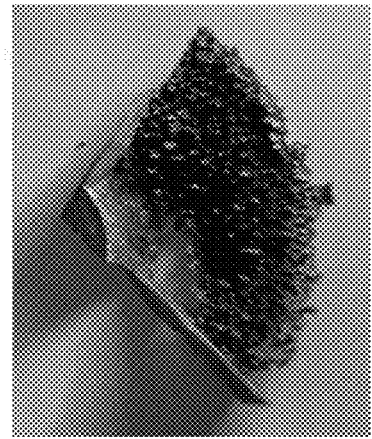
Figure No. 20
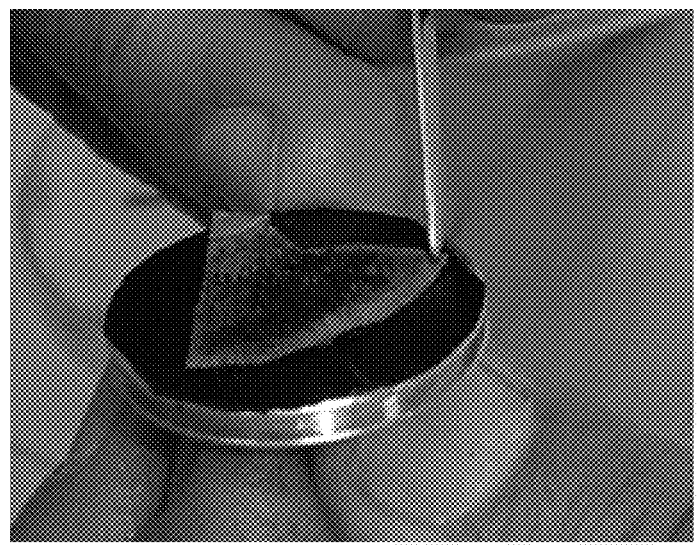
Figure No. 21

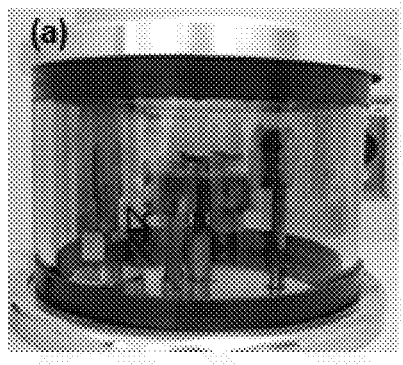
Figure No. 22
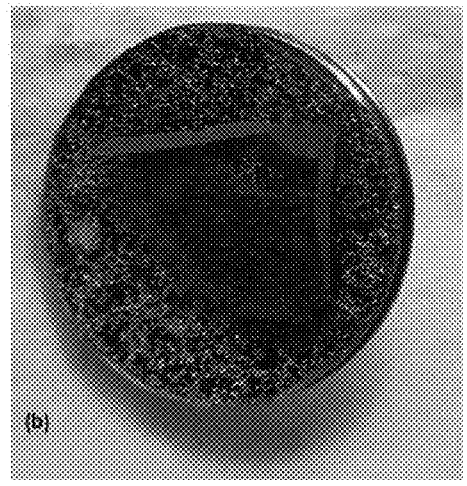
Figure No. 23
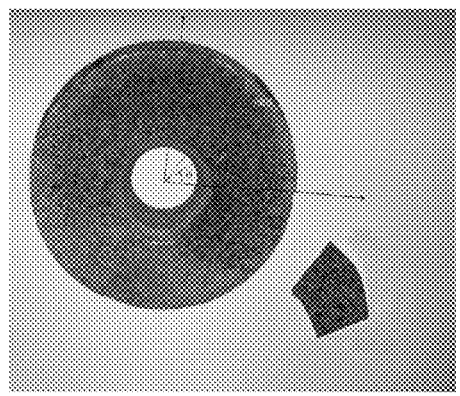 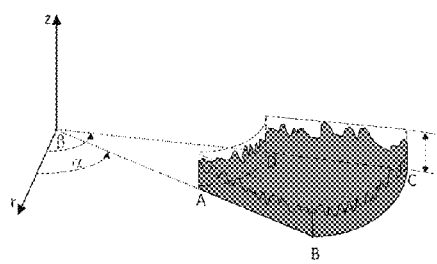
Figure No. 24

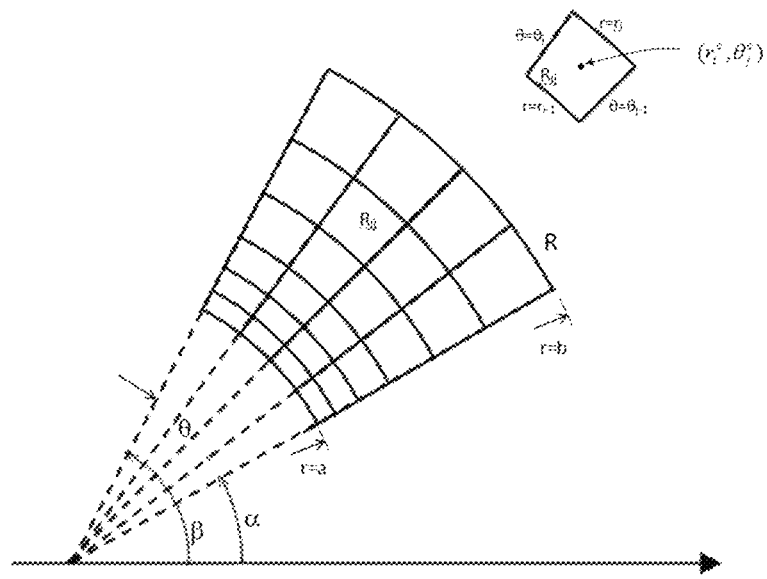
Figure No. 25
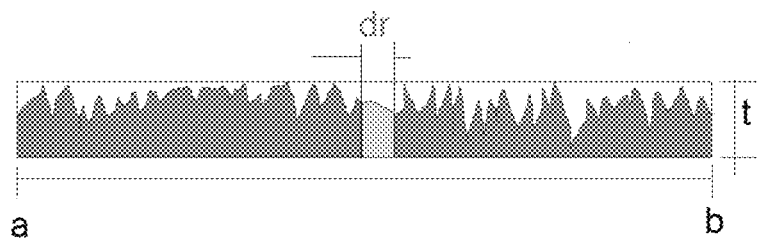
Figura No. 26
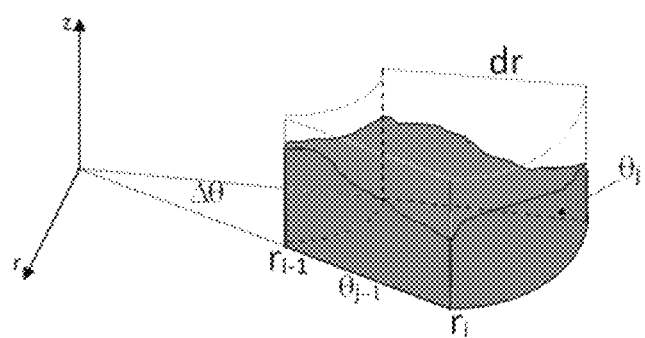
Figure No. 27

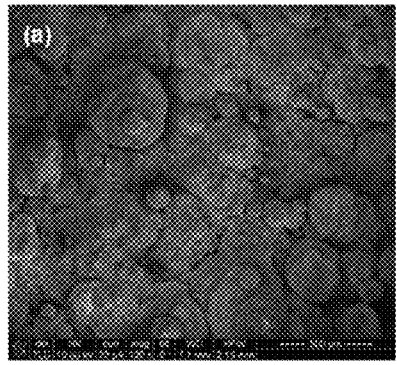 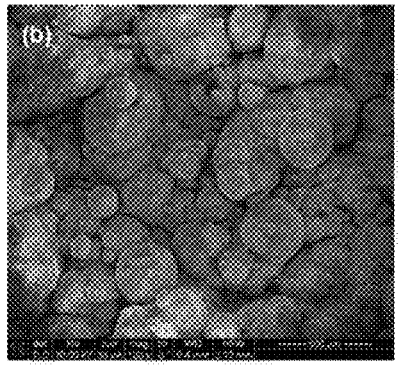 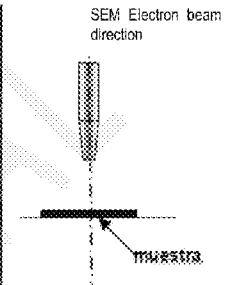
Figure No. 28　　　　　Figure No. 29
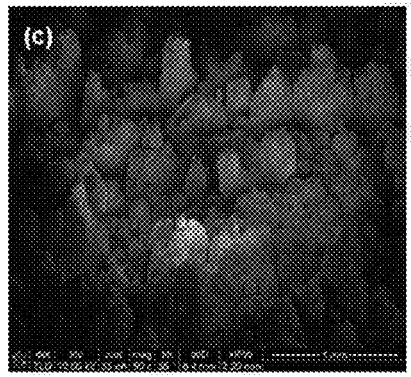 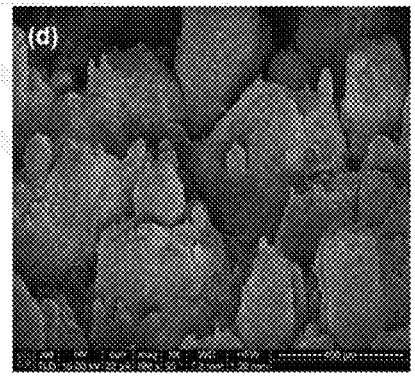 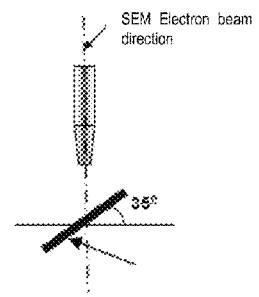
Figure No. 30　　　　　Figure No. 31

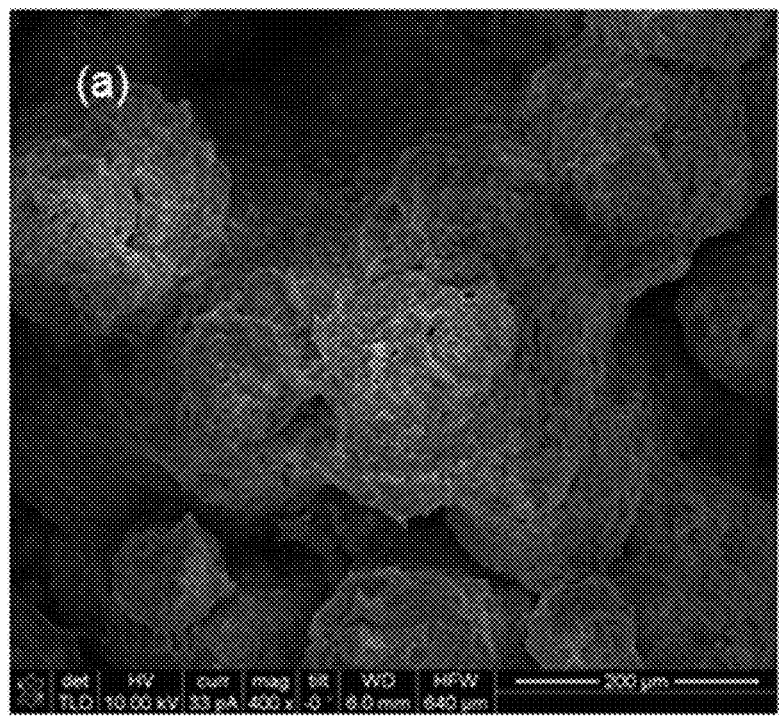
Figure No. 32
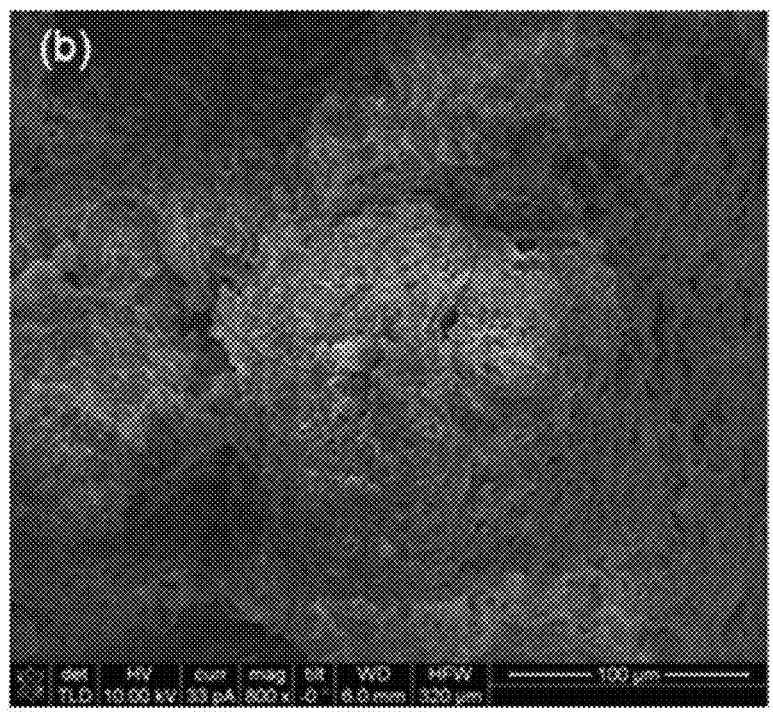
Figure No. 33

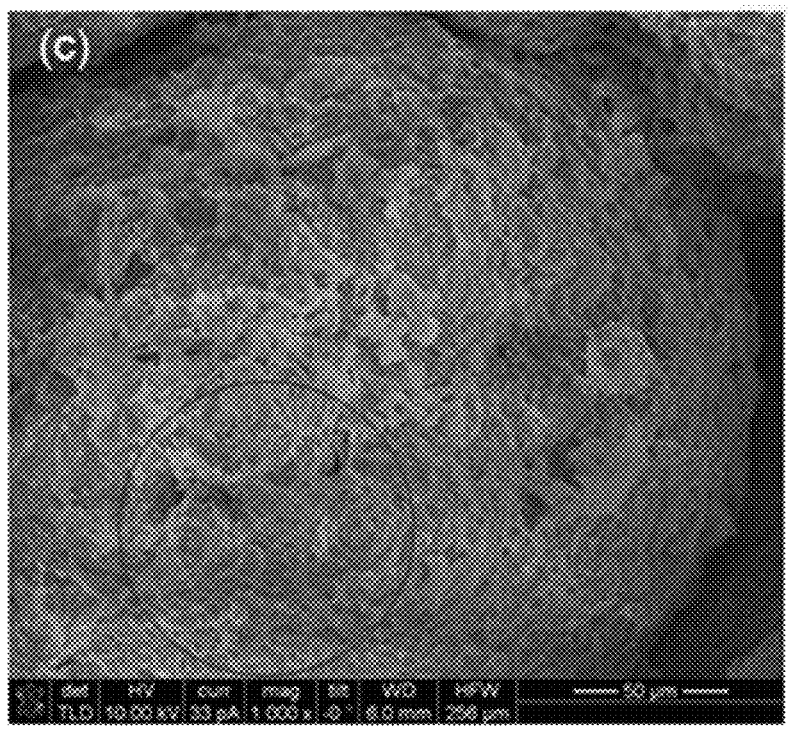
Figure No. 34
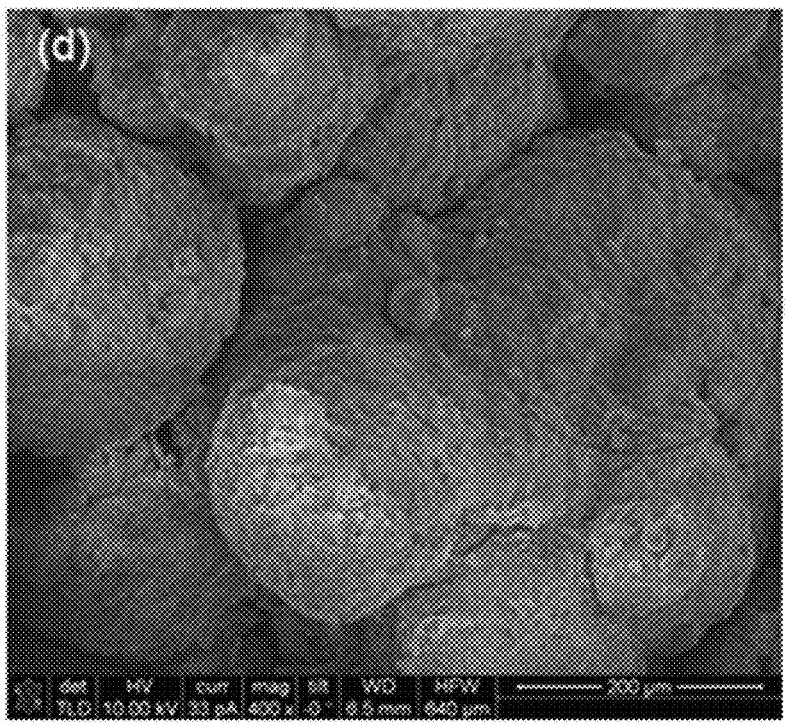
Figure No. 35

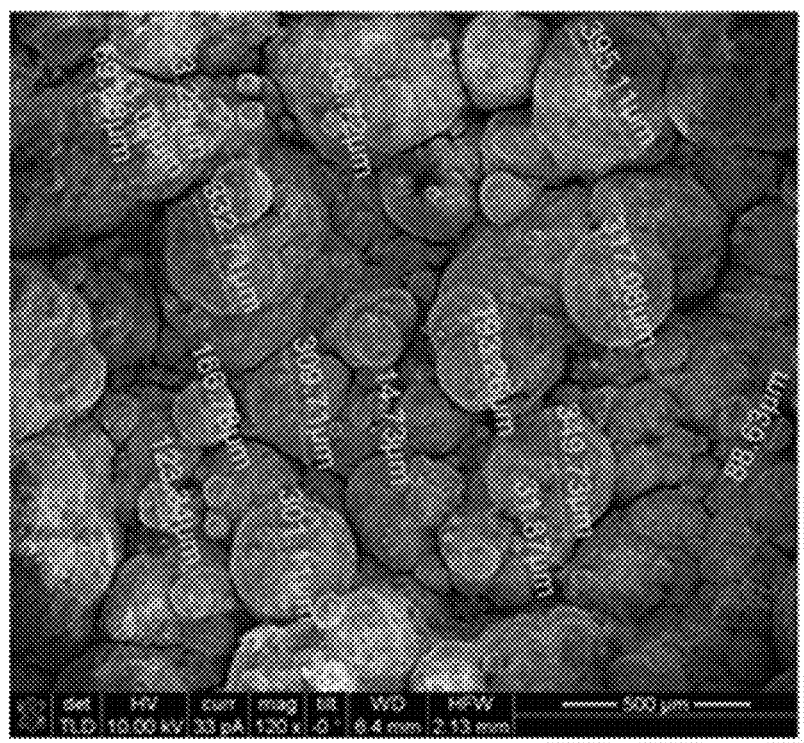
Figure No. 36
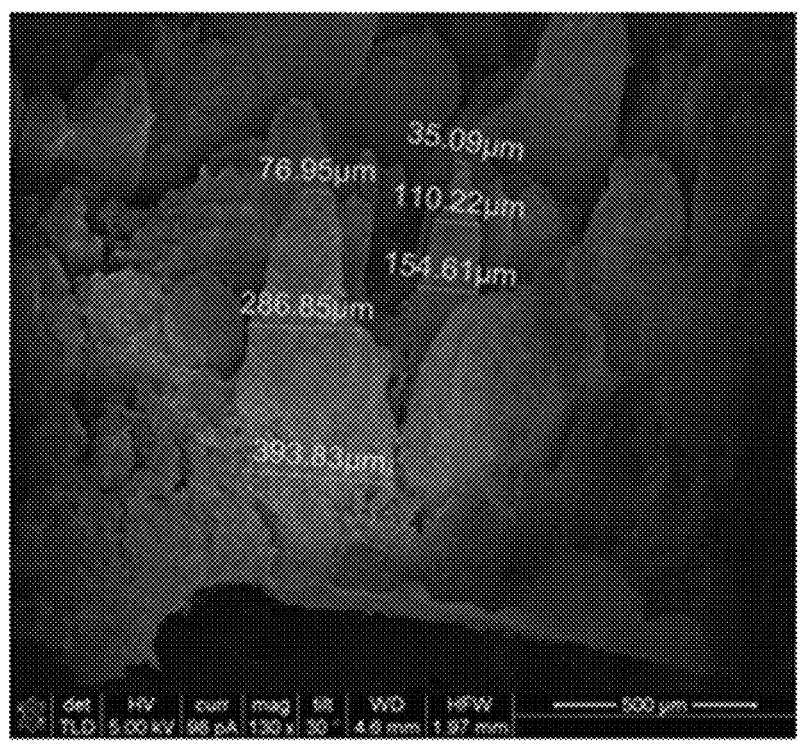
Figure No. 37

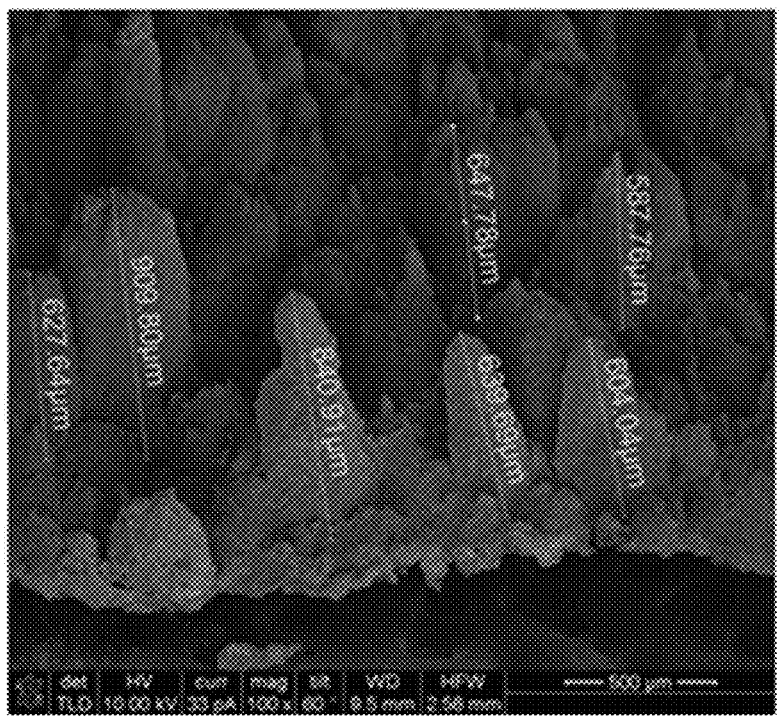
Figure No. 38
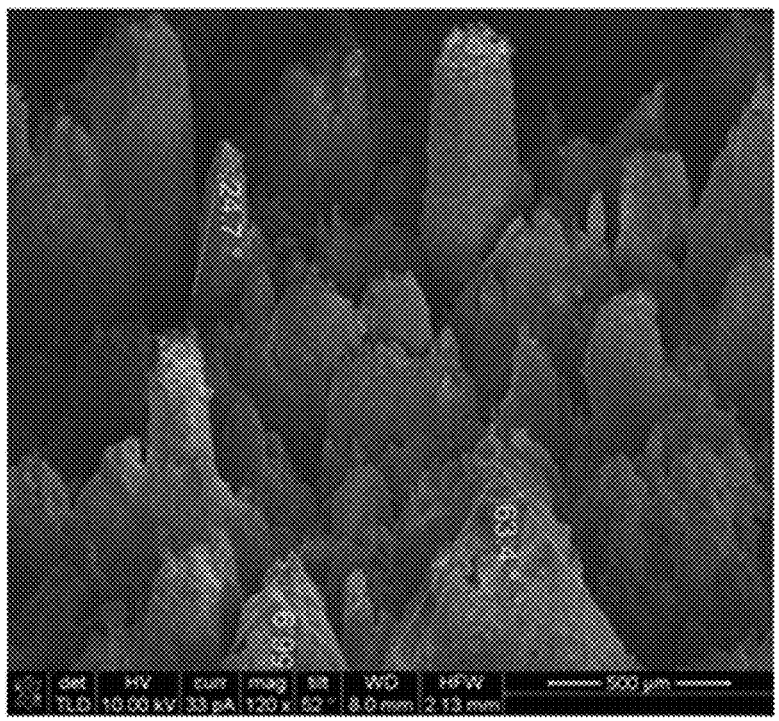
Figure No. 39

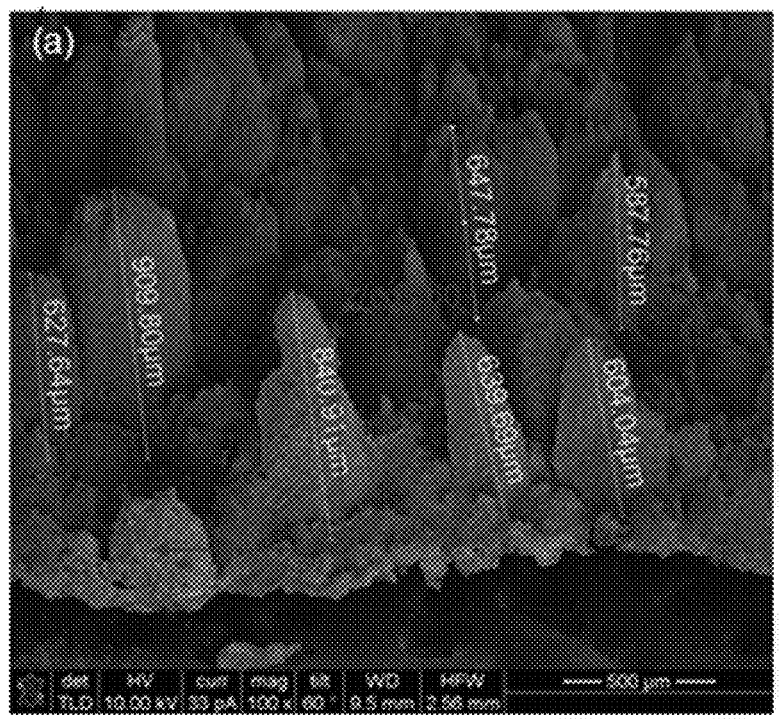
Figure No. 40
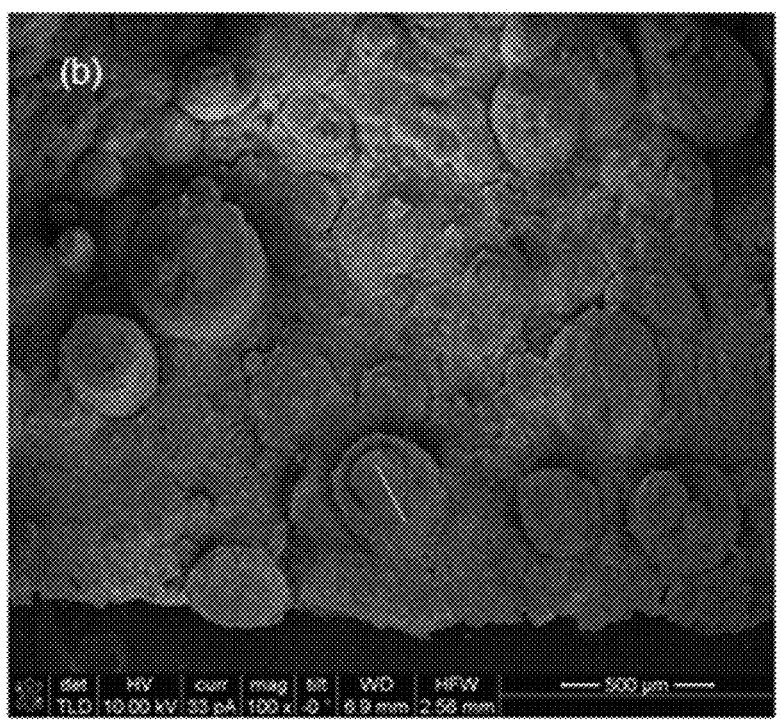
Figure No. 41

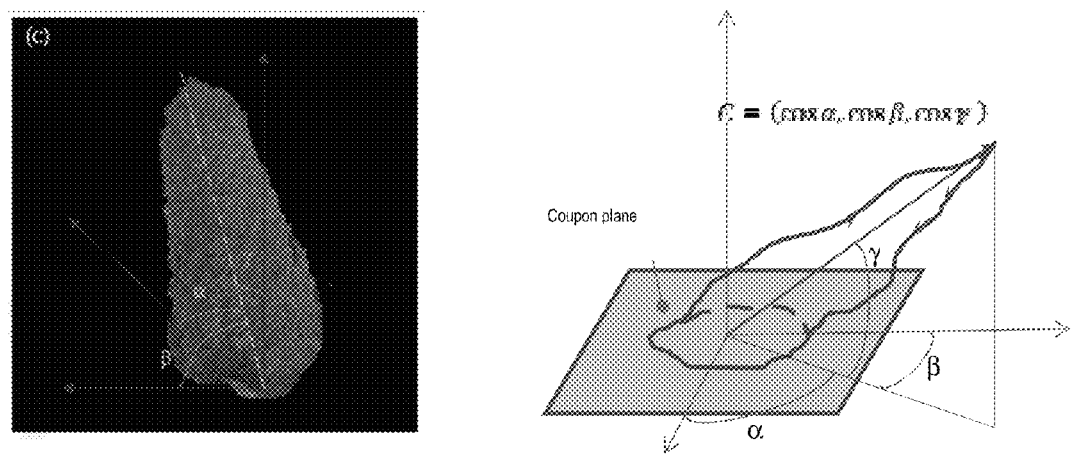
Figure No. 42
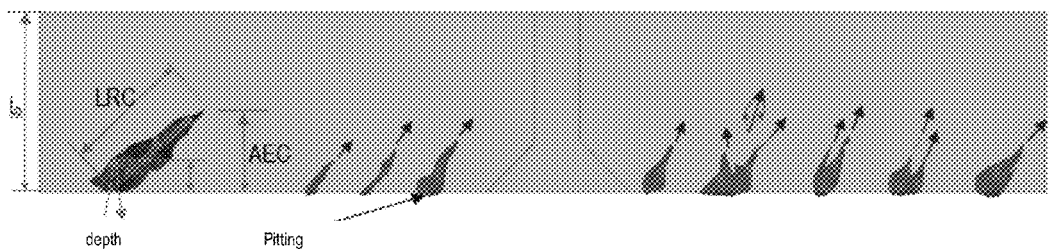
Figure No. 43

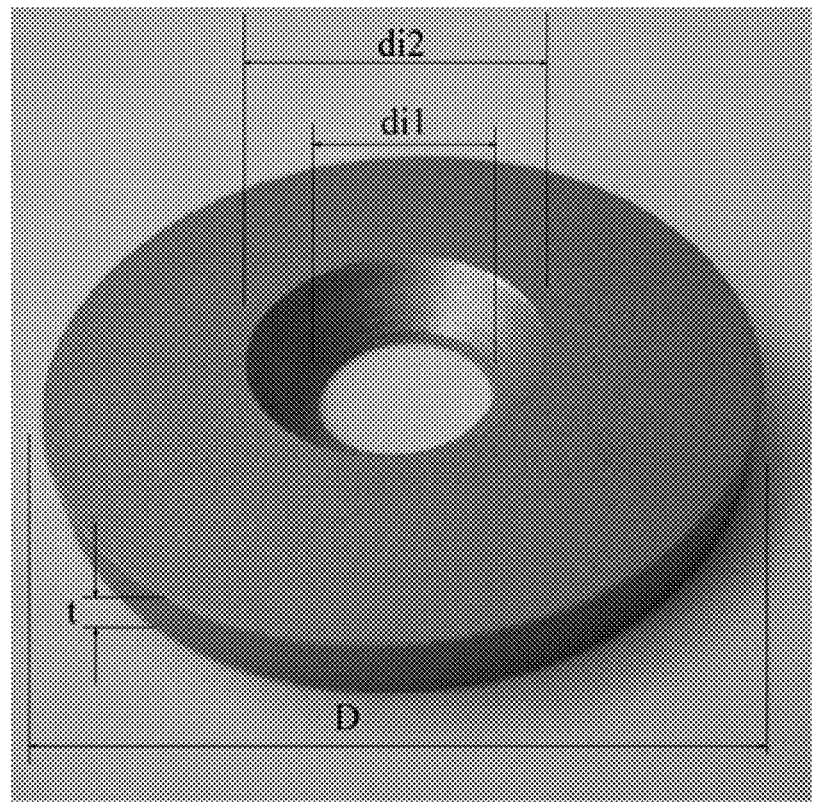
Figure No. 44
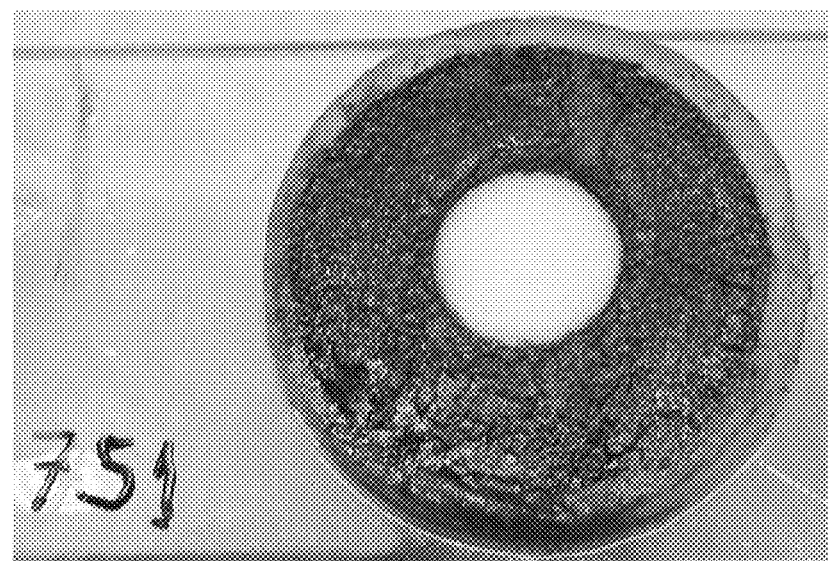
Figure No. 45

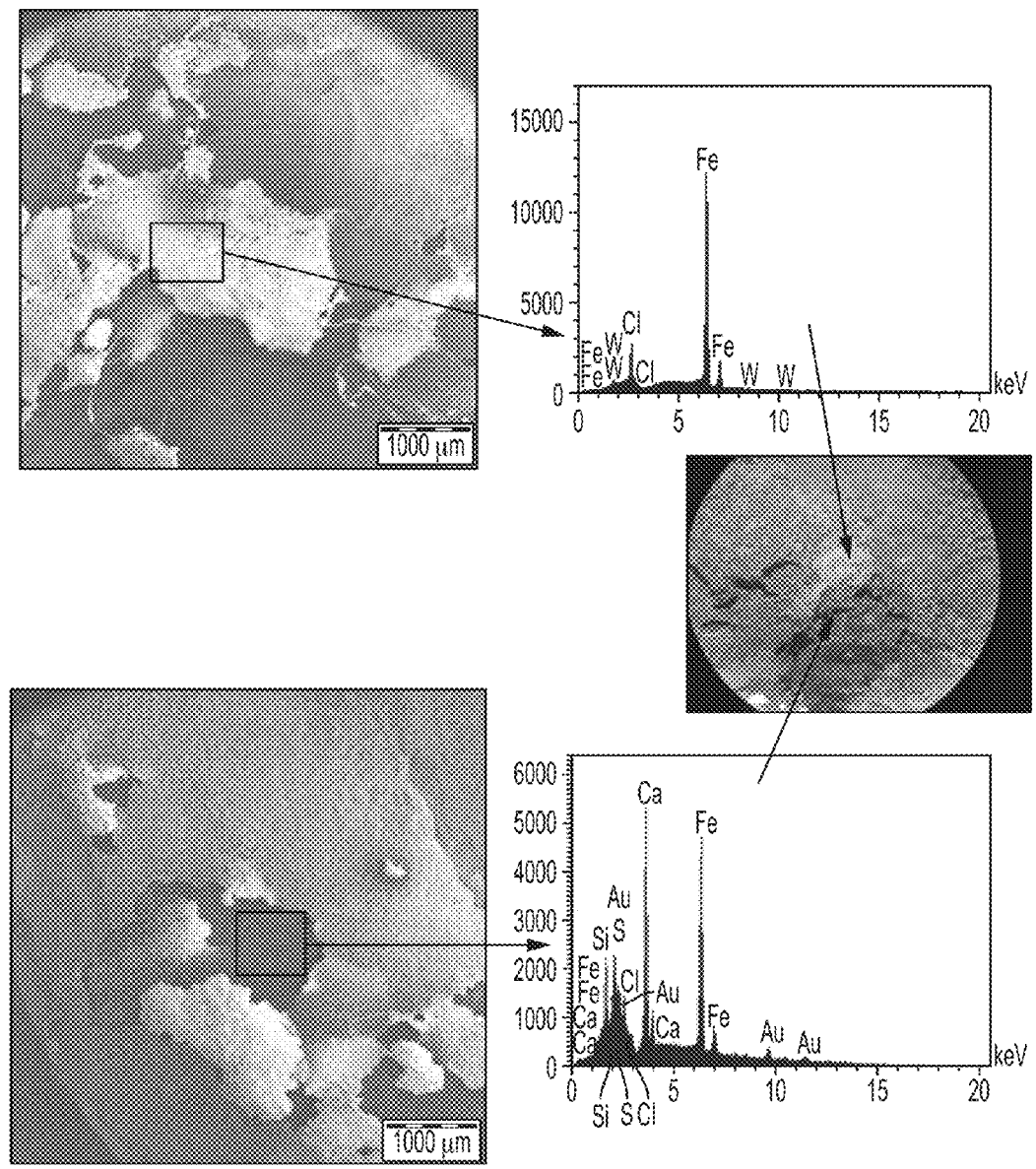
Figure No. 46

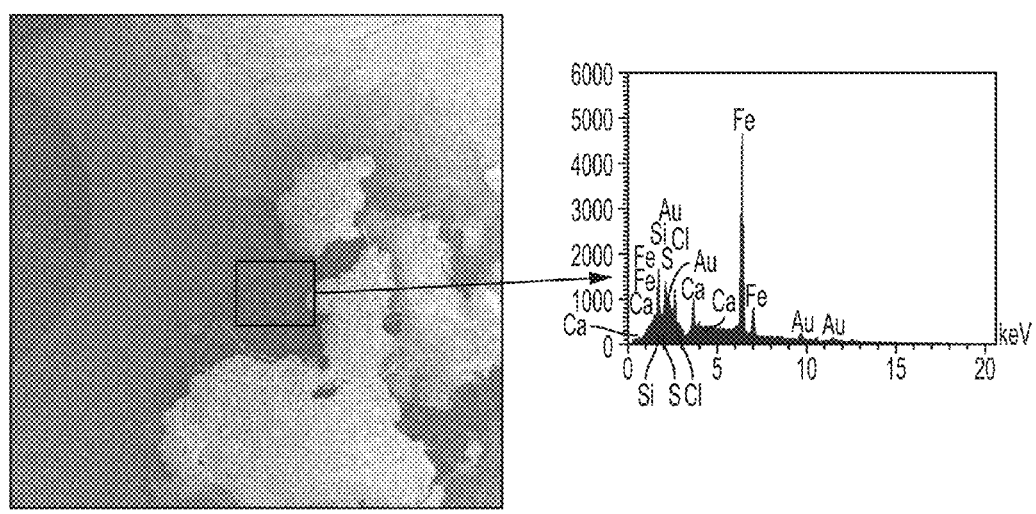
Figure No. 47

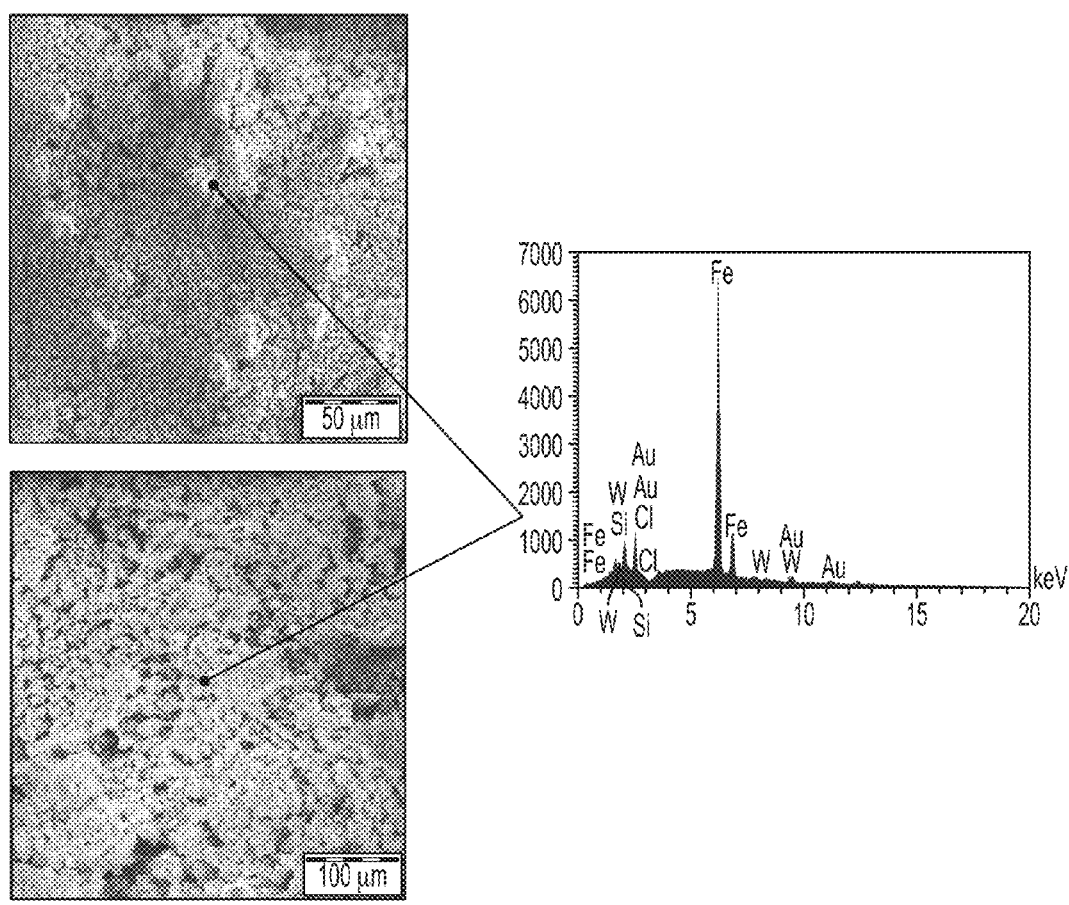
Figure No. 48

Figure No. 49

Figure No. 50

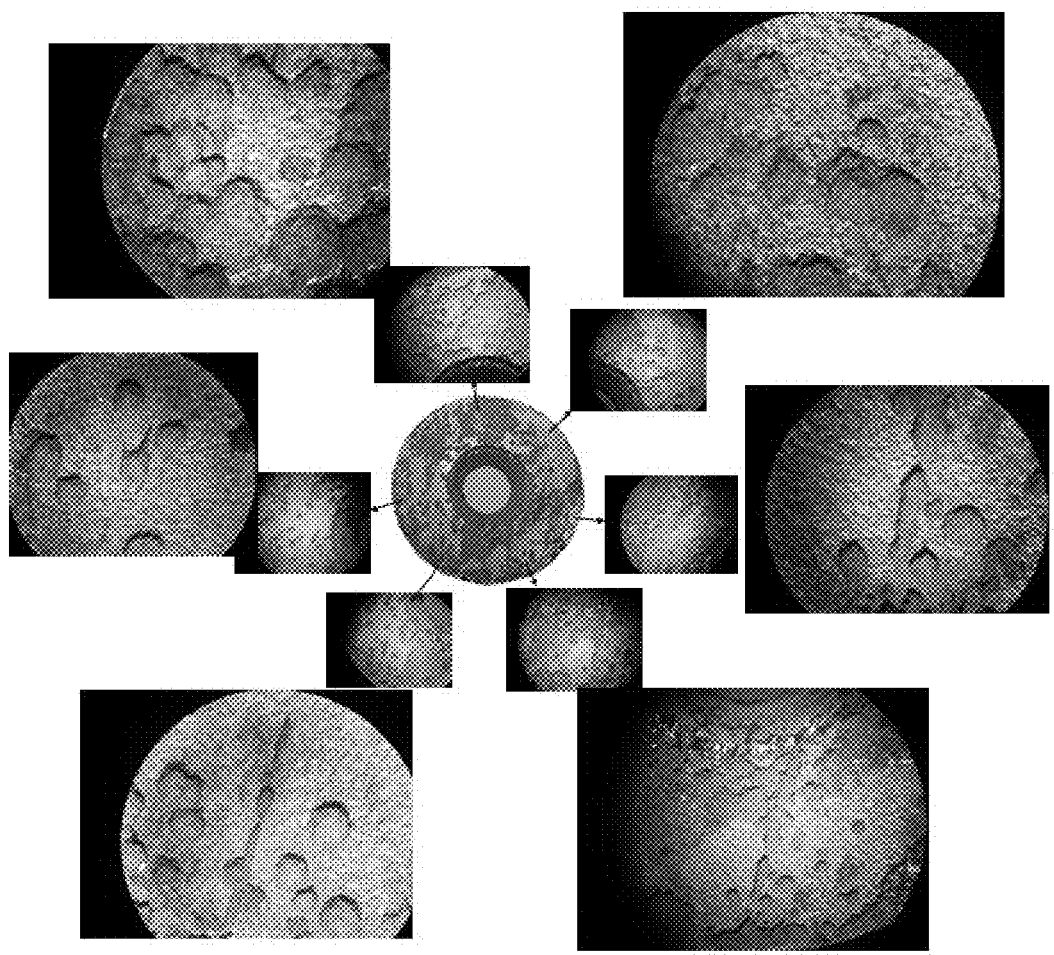
Figure No. 51

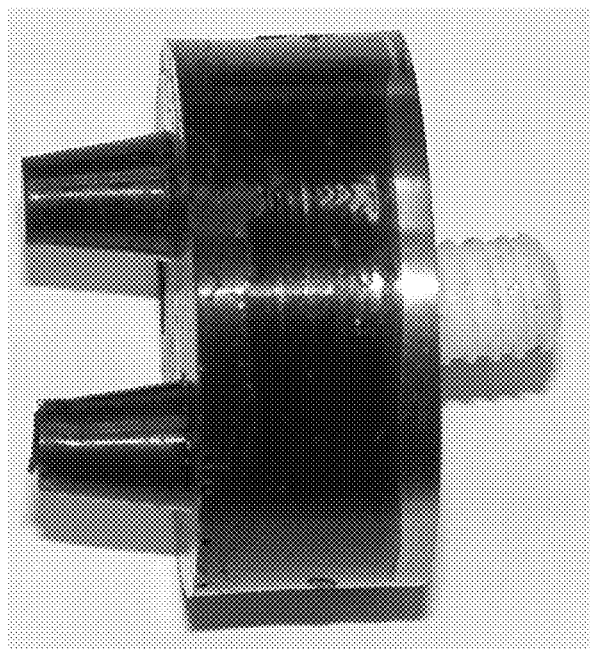
Figure No. 52

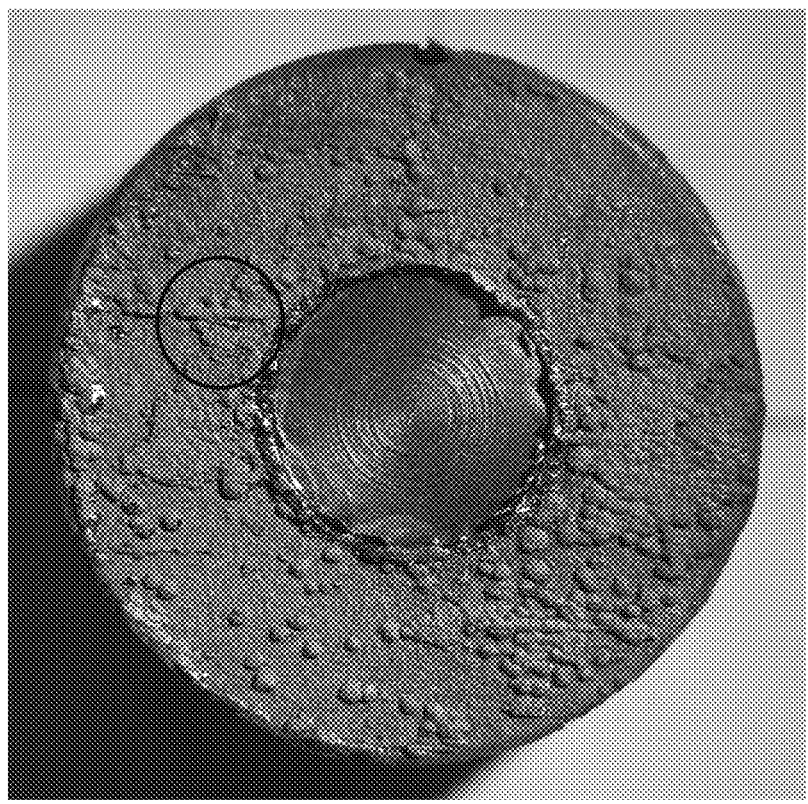
Figure No. 53

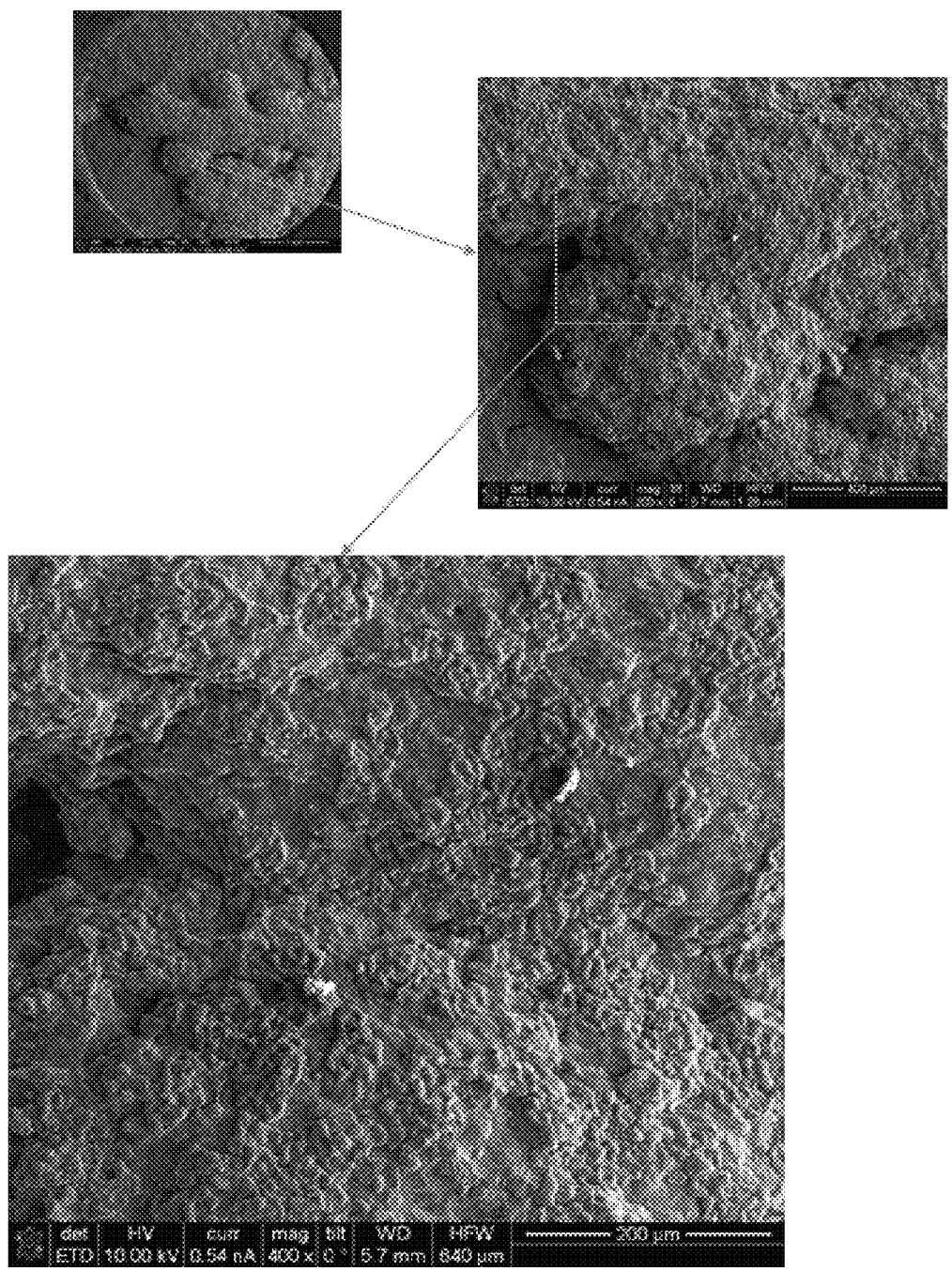
Figure No. 54

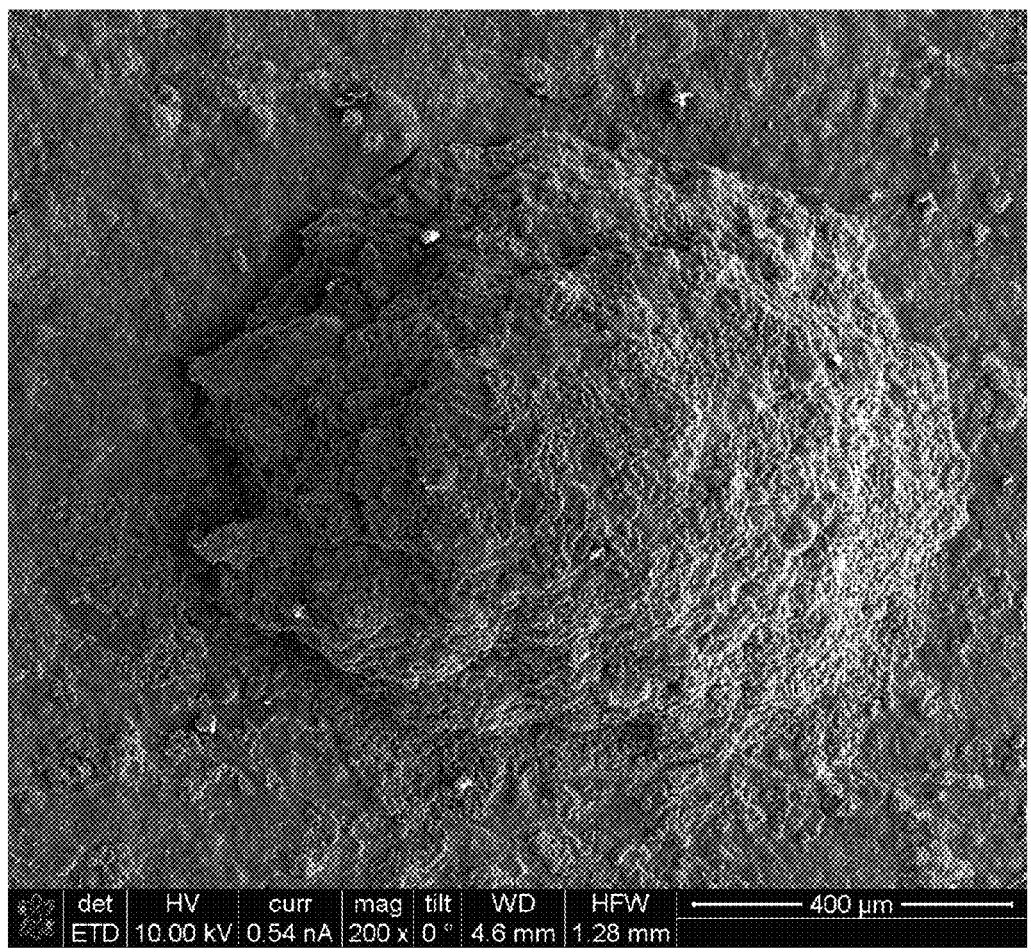
Figure No. 55

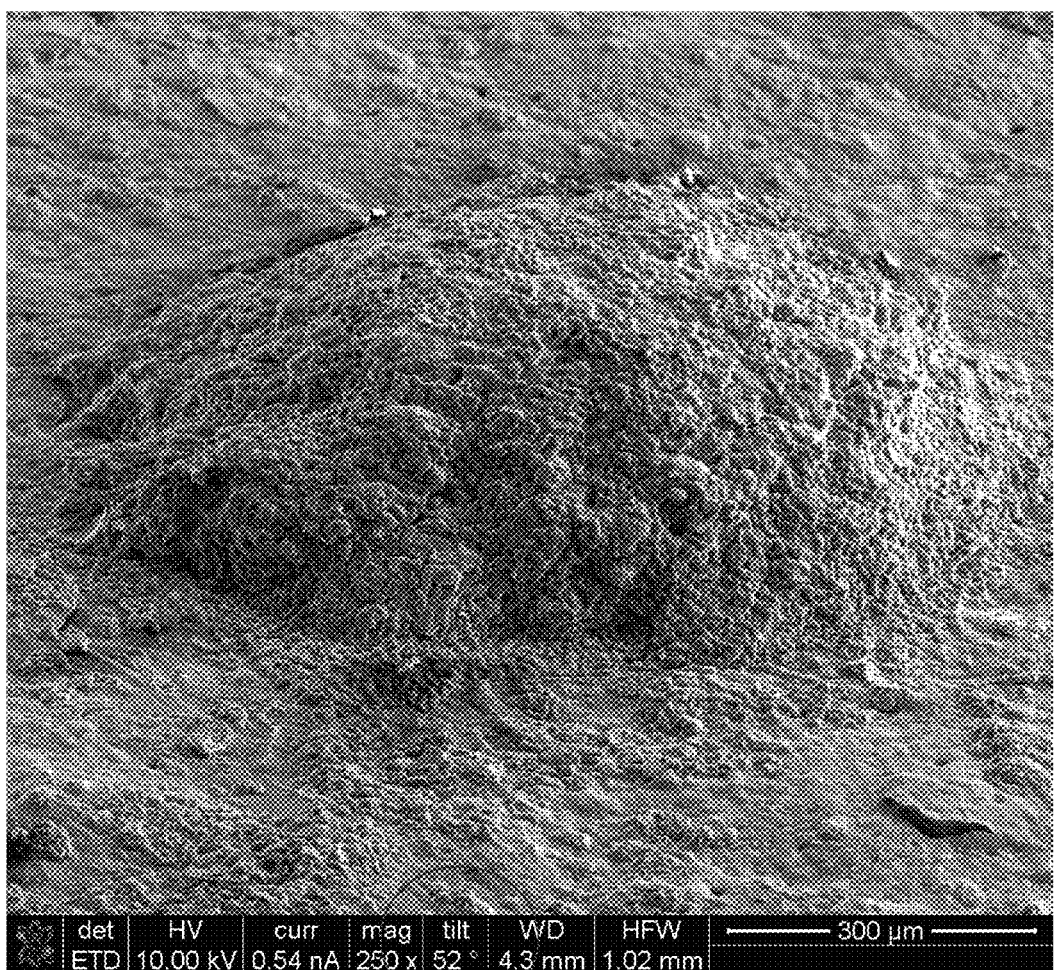
Figure No. 56

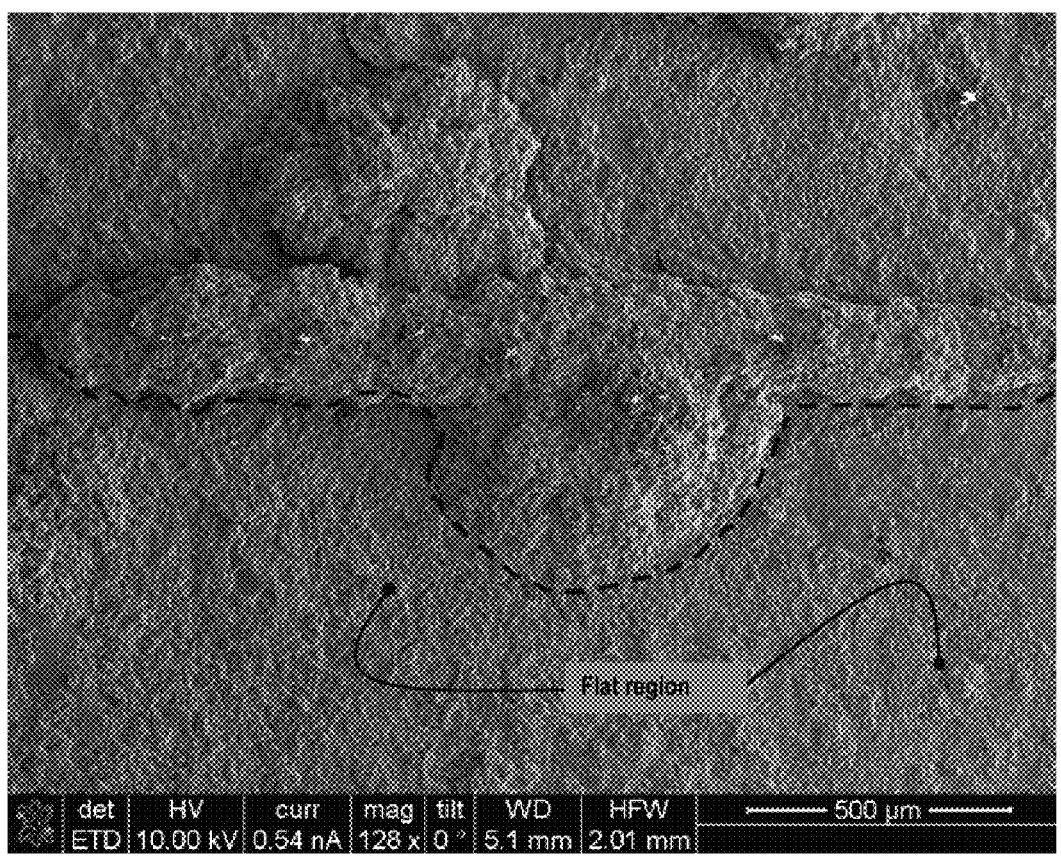
Figure No. 57

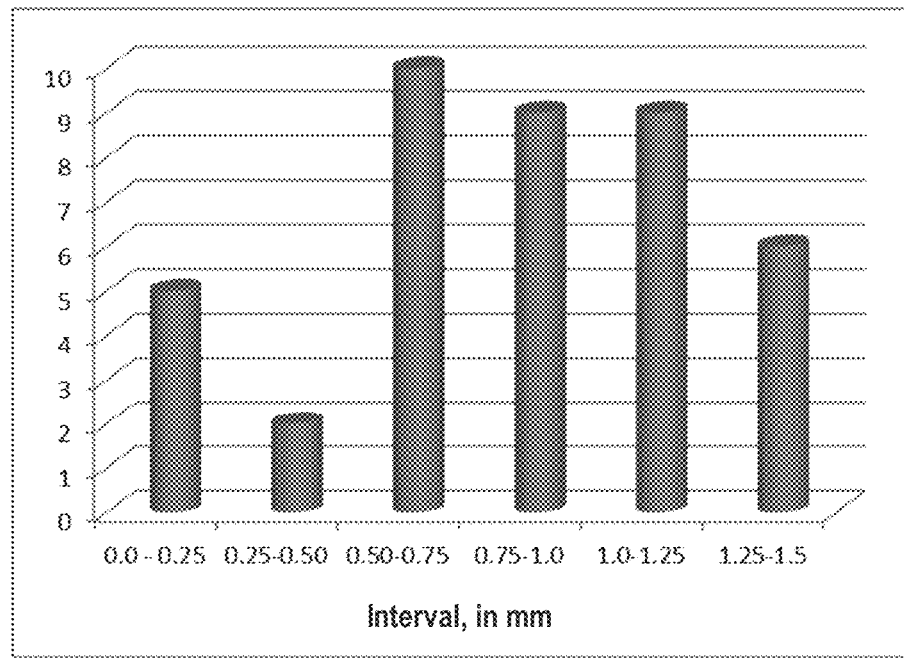
Figure No. 58
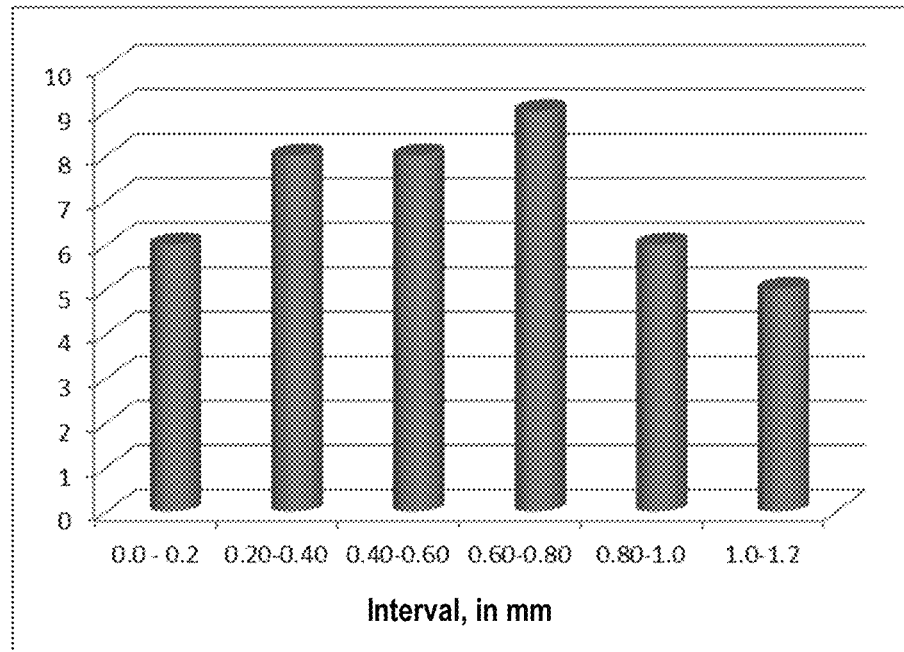
Figure No. 59

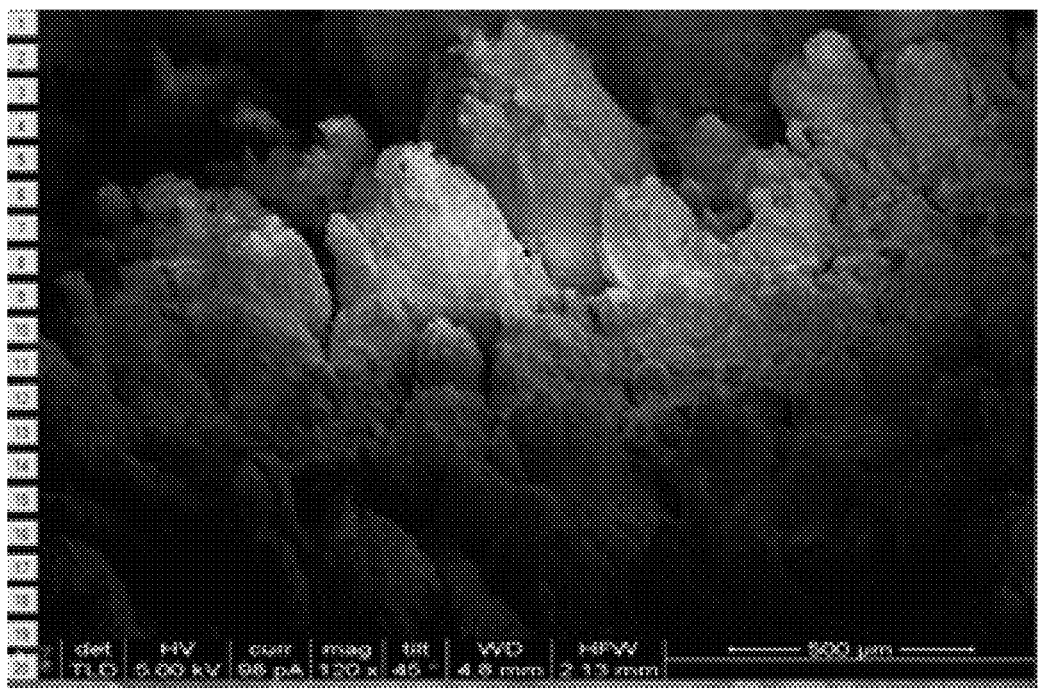
Figure No. 60

METHODOLOGY FOR THREE-DIMENSIONAL MORPHOLOGICAL AND QUANTITATIVE DETERMINATION OF MICRO AND NANOCAVITIES PRODUCED BY CHEMICAL AND MICROBIOLOGICAL CORROSION IN METALLIC MATERIALS

CROSS-REFERENCE TO RELATED APPLICATION(S)

This claims priority to Mexican Patent Application No. MX/a/2014/015591, filed on Dec. 17, 2014, the entire contents of which are fully incorporated herein by reference.

TECHNICAL FIELD OF THE INVENTION

The present invention refers to a procedure:
a) To determine the three dimensional morphology of micro and nano-cavities, as produced by chemical and/or biological corrosion in metallic materials, as well as the effective advance of the corrosion, the true length of the corrosion cavities and their associated parameters: vector field of corrosion, intensity of corrosion and the diameter/true-length ratio of corrosion by applying volumetric, gravimetric and analytic formulations and techniques of scanning electron microscopy (SEM).
b) To quantitative determine the rate of chemical and/or biological corrosion growth in metallic materials derived from their volumetric and gravimetric properties; and
c) To develop a graphic interface to access the numerical information and micrographs in a simple, user-friendly manner.

1. BACKGROUND

Corrosion is generically defined as the degradation of a metallic material through its interaction with its surrounding environment. A primary classification of this degradation, which occurs on the material's surface, is heat-dry, i.e. corrosion due to hot gases and humidity due to electrolytes in solution.

One type of aqueous corrosion involves the reaction of a metal surface with an electrolyte, also known as electrochemical interaction; this reaction produces a deterioration of the metals physical and chemical properties, which in turn accelerates its aging and destruction.

A relevant issue in this kind of corrosion phenomenon is the metal/electrolyte interaction. Here, an anodic dissolution of metals and the corresponding cathodic reduction takes place, producing a redox reaction this way. What also happens is the adsorption and formation of oxide layers, which can significantly reduce the corrosion rate by the inhibition of the chemical reactions existing in the corrosion process. The electrolyte is the place in which the subsequent chemical reactions take place, and the migration and diffusion of the corrosion byproducts and species involved in the corrosion process occur.

Another important mechanism responsible for corrosion is that induced by microorganisms (MIC), which is a process where microorganisms are involved (bacteria, fungus, algae); they either initiate, facilitate or accelerate the corrosion process. In the USA, the cost of corrosion affectation represents 3.1% of the gross domestic product of the country, and 40% of the internal corrosion in oil industry pipes is attributed to microbial activity.

The states of stress and deformation of materials also play an important role in corrosion phenomena. Different types of corrosion may occur depending on the redox reactions at the metal surface. Here, two types of corrosion are classified into those with and those without mechanical stresses involved.

Pitting corrosion involves no mechanical stress. It is especially observed in austenitic stainless steels in the presence of certain anions in electrolytes (chlorides and bromides). Pitting corrosion is caused by the local destruction of the passive protective layer of the metal with the formation of a small corrosion anode (pit). For low carbon content steels, pitting corrosion is commonly caused by the presence of sulfides in the alloy, combined with the action of bromide and/or chloride anions, which produces a low pH environment in the volume around the pit, further accelerating the corrosion process. Corrosion by erosion, on the other hand, does involve mechanical stresses and is observed in pipes transporting liquids. This type of corrosion appears when the flow speed exceeds a certain limit, due to local turbulence, or when there is formation sand flowing in the fluid. In this corrosion phenomenon, the passive surface of the metal is detached by the flow, leaving the metal bare, uncovered and susceptible to corrosion by the transported liquid.

Techniques for Corrosion Measurement

Various techniques exist for the measurement/analysis of corrosion, each based on different physical, chemical and biological phenomena, and aimed to obtain specific information to describe the corrosion in the studied system. Table 1 presents a non-exhaustive classification of corrosion tests based on the information and technique used.

TABLE 1 techniques and tests to measure corrosion

| Classification | Information/technique |
|---|---|
| Tests based on emission of signals: acoustic, magnetic and electrical current | Ultrasound<br>Acoustic Emission<br>Eddy Current/Magnetic Flux<br>Smart pigs |
| Chemical, biochemical and microbiological analyses | pH Measurement<br>Gas Dissolved ($O_2$, $CO_2$, $H_2S$)<br>Metallic Ions counting ($Fe^{2+}$, $Fe^{3+}$)<br>Microbiological Analysis |
| Information of the operation | Temperature<br>Velocity or Flux rate change<br>Pressure<br>pH |
| Electrochemical techniques | Potential Measurement.<br>Potentio-static Measurement.<br>Potentio-dynamic Measurement.<br>A.C. Impedance. |
| Monitoring in the corrosion environment. | Corrosion Coupons<br>Biocoupons or bioelements<br>Electric Resistance<br>Linear Polarization<br>Hydrogen penetration.<br>Galvanic Current<br>Sand erosion monitoring |
| Techniques based on electromagnetic signals processing. | Radiography<br>Thermography.<br>Laser profilometry.<br>2D Scanning electron microscopy.<br>Transmission electron microscopy.<br>Atomic force Microscopy<br>Optic Microscopy.<br>Ellipsometry. |

Tests Based on the Emission of Acoustic, Magnetic and Electric Current Signals.

These tests are based on the emission and/or reception of: acoustic signals of low and ultrasonic frequencies, electrical current and magnetic fields. By their nature they are known to be non-destructive and require devices to emit and/or capture these types of signals. The information obtained includes; detection of the existence and depth of cavities within the materials and the determination of the corrosion affected surface morphology in three dimensions, although the detection of a pit depth is limited to the depth that the signal can reflect back to a detector, thus restricting the information on the true shape of the cavity.

Chemical, Biochemical and Microbiological Analyses

These tests are based on the measurement of existent elements which allow, cause or are byproduct of corrosion in metallic surfaces. There exist both; laboratory and field quick tests. These tests mainly determine pH, dissolved gases content, presence of metallic ions, sulfate-reducing microorganisms, reducers of Fe and Mn, oxidizers of sulfur, fermenters and producers of exopolym ers.

Information of the Operation.

This information provides direct or indirect evidence of the existence of areas subject to corrosion; among them are the velocity or change in flow velocity, existing thermal gradients, pressure or pressure gradient and the acidity/alkalinity of the flow environment.

Electrochemical Techniques

These techniques are based on the electric potential difference between two or more electrodes in the metal, which is affected by the corrosion between them. In this way, through the analysis of the potential decay on a metal surface, one can produce a map of position and extent of the corrosion.

Corrosive Environment Monitoring.

Monitoring of corrosion is vital to the oil and gas industry. It permits preventive and corrective actions to be carried out, avoiding much greater potential losses. In "Corrosion in the oil industry", Oilfield review, Shlumberger V6(2) April 1994, Brondel, E. et al describe techniques of corrosion monitoring in the petroleum industry.

Gravimetric monitoring techniques of the corrosive environment are based on the measurement of average corrosion using corrosion coupons. A coupon mass is weighed before and after exposure to the corrosive environment; in this way it is possible to obtain the percentage of material lost over a known period of time. The methodology for the preparation of the test mass samples and the subsequent evaluation of the corrosion by this technique is documented in ASTM G1-90 (2003) "Standard Practice for Preparing, Cleaning, and Evaluating Corrosion Test Specimens".

Biocoupons or bioelements, on the other hand, permit, after being exposed to the corrosive environment in the field, the extraction and identification of biological entities that induce corrosion. This is achieved through the application of traditional microbiological techniques or molecular biological methodologies. On the other hand, it is possible to determine the characteristic morphology of the microbiological corrosion which presents itself as small pits of varying depths and can cause damage and fracturing of metallic materials. Techniques of electron microscopy are used for the analysis of this type of corrosion.

Measurement of the lineal polarization resistance. This method quantifies the polarization resistance of an electrode exposed to a corrosive environment in order to determine the corrosion electric current. By considering the linear voltage-current response of a corroded element over a small range of values, the gradient of the linear section is the polarization resistance. This resistance is inversely proportional to the corrosion current, thus allowing calculating the rate of corrosion.

With respect to this technique, it has been reported that the addition of Nitrogen enhances the resistance to pitting corrosion in austenitic steels, reducing the potential of pitting corrosion in chlorine solutions or diminishing the mass loss in immersion tests in $FeCl_3$. Therefore the presence of nitrogen is an important indicator of these materials resistance to pitting corrosion.

Electrochemical potentials. Pitting corrosion is also studied by electrochemical potentials and optical images. It allows evaluating this kind of corrosion and galvanic behavior of highly austenitic stainless steel alloys.

Method of Eddy Currents. This measurement technique is based on changes in the impedance of a sensor coil, due to defects in the material continuity, as an electric current passes through the material. This technique is especially useful for detecting small fractures or pits. Devices using the eddy current method have been used to identify and quantify intergranular corrosion (DOS) and the sensitivity of specimens of stainless steel (AISI 316) to this type of corrosion. The categories of sensitivity are based on "fracturing severity" after a bending test. They are, in increasing order: test specimen unaffected, fissured, fractured and broken. It has been observed that the amplitude of the Eddy currents increases with DOS.

Erosion of pipes by sands flow can be quantitatively estimated through expressions that involve velocities and angles of impact, density and ductility of the materials involved.

Techniques Based on Electromagnetic Signals Processing

These techniques are based on the use of electromagnetic radiation to analyze the morphology and composition of a sample. The precision of the obtained signals differ depending on the wavelength of the radiation utilized. Visible light radiation is exploited in both, optical microcopy and ellipsometry. Monochromatic visible light in the form of laser radiation, both in fixed and mobile devices, permits scanning of the surface of a pipe or sheet of metal in a way analogous to the acoustic technique. It is possible to use these techniques to measure the thickness of a passive oxide layer or to obtain the topography of a surface. Laser confocal microscopy allows to study the microorganisms existing within a corroded area. By scanning electronic microscopy, a beam of electrons interacting with the atoms of a material allows to define with great precision the corroded surface morphology. Structural and atomic composition of a specimen can be characterized in standalone spectrometers or spectrometers associated to electron microscopes. Electromagnetic radiation in the X-ray range permits the identification of the elements and compounds that make up a specimen attacked by corrosion.

Thermographic systems make use of radiation in the infrared to detect electrical systems that have experienced corrosion; the increase in electrical resistance of the damaged connections causes an increase in the local temperature around them Corrosion in the Oil and Gas Industry Corrosion in the oil and gas industry is present in nearly every component of every stage, from exploration and exploitation of hydrocarbon deposits to refining and production of the oil and gas derivatives. Table 2 presents a non-exhaustive list of conditions of corrosion and their potential solutions.

TABLE 2

Causes of corrosion in the oil and gas industry

| Cause of corrosion | Methods of prevention and mitigation |
|---|---|
| Corrosion of surface equipment due to rain, condensation and sea-breeze dispersion in presence of oxygen. Corrosion products and pitting in internal and external piping surfaces. | Protection with zinc-rich paints, use of inhibitors, biocides, cathodic protection. Cleaning pigs, spheres, moisture traps and use of sleeves. |
| Corrosion in the sea wave zone | Overdesign of metallic elements thickness, use of anti-corrosive coatings and installation of cathodic protection systems with sacrificial anodes. |
| Overloads due to the accumulation of crustaceans and algae, waves pounding and accidental loads of low frequency, tides and operational loads, cavitation effects. Increased pitting corrosion under induced stresses enables the propagation of fractures leading to structural failure. Corrosion of drilling bars. | Modeling and inclusion of these loading states and forces in the structural design to mitigate the losses due to corrosion. |
| Structural supports of self-elevating platforms, immersed ducts, distillation towers attacked by sulphate reducing bacteria (SRB). Water injected for secondary production, together with formation water cause corrosion in the steel pipes due to the high concentration of salts such as chlorides and the presence of hydrogen sulfide, the origin of which is microbiological. | Cathodic protection, removing agents containing sodium chromate, zinc chromate and sodium nitrate to remove the $H_2S$. Inhibitors of bio-films, such as triazine-based compounds are used as biocides for controlling bacteria. |
| Galvanic corrosion due to the union of two or more elements composed of different metals. | Cathodic protection. |

Corrosion monitoring is very relevant for the oil and gas industry since it allows for preventive and corrective actions to avoid big financial losses. In "Corrosion in the oil industry, 1994" Brondel, E. et al, 1994 "Corrosion in the oil industry". Oilfield Review: 6(2), the authors describe some corrosion monitoring techniques in the hydrocarbon industry.

Microscopy Based Characterization of Pitting Corrosion

These types of corrosion have been studied with various microscopy techniques: Optical microscopy helps to determine the presence or absence of corrosion films and cavities caused by pitting. In the latter case, it permits the measurement of the cavities surface areas in the material and therefore allows determining the statistical distribution of those cavities surficial diameters. In addition, it permits the identification of coalesced and/or isolated cavities and their distribution on the metal's surface, as well as to identify surface fracture patterns; it also helps to determine the existence of inclusions and defects and, by manipulating the focus, allows making a rough estimate of the depth of pits.

Raman microscopy allows the identification, by spectroscopy analysis, of the specific chemical species produced in the corroded material. It also helps to study dynamic systems, such as the phenomenon of transport and distribution of chromates to active pits and the consequent formation of corrosion products on different timescales, from milliseconds up to several days. It also allows the determination of the chemical nature of these products by comparing their spectra with other spectra from known synthetic materials.

Scanning electron microscopy (SEM) provides additional advantages over the capabilities of light microscopes for the characterization of pitting corrosion. These instruments have a far greater resolution, down to 2 nm even under low vacuum; their magnification capabilities above 1,000,000× are unrivalled; all these features combined with its large focal depth made of SEM a standard tool in metallurgical science. Supported on their peripheral spectroscopy and nanomanipulation systems, these instruments help to identify the origin of the corrosion by noting the type of corrosion, the deposits found in the attacked area and the corrosion byproducts. For example, the presence of microorganisms, preserved in Glutaraldehyde, can be studied by electronic microscopy. The use of SEM in the characterization of pitting corrosion has evolved with the advent of new tools and techniques. Table 3 depicts the evolution on the characterization of this corrosion form using scanning electron microscopes.

TABLE No. 3

Evolution of the characterization of pitting corrosion using scanning electron microscopy (SEM).

| SEM technical features availability | Electron microscopy Output |
|---|---|
| Field-emission SEM and secondary electrons | surface corrosion micrographs, FIG. No. 1 [(1)] |
| SEM with backscattered electrons detector | surface corrosion micrographs with phases identification and microstructure, FIG. No. 2[(2)] |
| SEM and probe microanalysis (EPMA) | Identification and concentration of elements, FIG. 3[(2)] |
| SEM with secondary electrons | Observation of the pitting corrosion spread, by tilting the stage, at the specimen edge. FIG. No. 4[(3)] |
| SEM with secondary electrons | Observation of the pitting corrosion morphology by physically sectioning the specimen, FIG. 5[(3)] |
| Field emission Dual-Beam SEM with ion and electron beams and micro EDS. | Observation of pitting corrosion morphology by sectioning the observation area with an ion beam, FIG. No. 6[(4)] |
| Dual-Beam SEM with field emission and electron beam | Observation of the interface of corrosion products on steel in an ion-beam sectioned area, FIG. No. 7[(4)] |
| Field emission Dual-Beam SEM with ion and electron beams and micro EDS. | Spatial characterization of elements existing at the pitting corrosion zone, FIG. No. 8[(4)] |
| Tunneling microscopy with an electrochemical unit, under controlled environmental conditions. | In-situ electrochemical studies with topographic characterization and phase identification, before and after the corrosion attack, FIG. No. 9[(5)]. FIG. No. 9 in section A shows the surface initial conditions and, section B shows the same surface after two cycles of the process. |

Table No. 3 shows how SEM techniques for the characterization of pitting corrosion have substantially developed in the last decade, through the arrival of observation in low-vacuum, WDS spectrometry and the inclusion of ion beams in these systems. However, morphological, textural, dimensional and directional characterization of the cavities has not been adequately addressed yet.

Use of Polymers

To the knowledge of the authors, the use of polymers to characterize corrosion pitting in test specimens has not been implemented in the oil and gas industry. N. Chawla et al., in 2003, in their document "Three Dimensional (3D) Characterization and Modeling of Porosity in Powder Metallurgy (P/M) Steels" utilized a technique involving epoxy resins to study the porosity of metallic alloys. Here, they describe a procedure involving microscopy imaging of a steel specimen previously impregnated with resin; afterwards, it was sequentially polished and photographed. The outcome was a series of images, which were integrated together by reconstruction software to obtain a digital object in three dimensions. One of the limitations of this procedure is the necessity for interpolation between each image, which smoothes out the porosity texture and thus does not correctly reproduce the original porosity system; In addition, an optical microscope was utilized to obtain the images; this limits the resolution, magnification and ultimately, the images precision.

According to the state of art, little have varied the procedures for polymer injection, this is particularly true in the morphological study of the pores present in rocks as can be observed in Pittman, E. D., y Duschatko, R. W. 1970 paper: "Use of pore casts and scanning electron microscope to study pore geometry", Journal of Sedimentary Petrology. 40(4), 1153-1157). In the case of metals, the direct application of polymeric molds has been focused on the morphological characterization of the microporosity of fabricated alloys. However, nothing has been done to determine the morphological properties of a metal exposed to corrosion on the micro and nanometric scales and to quantify their corrosion rate. The advantages of using polymeric resins to obtain molds of the cavities caused by corrosion, is that the morphology of these cavities can be studied in great detail in three dimensions; in fact, the precise shapes of the micro- and nano-cavities, which cannot be obtained and measured by the aforementioned methods can be determined using this technique. For example, in the use of ultrasound or scanning laser methods, the maximum accessible depth depends on the orientation of the cavities with respect to the sensor; this fact limits the maximum depth that those devices can reach. In addition, the cost to acquire transversal sections by ion beam cutting, in terms of time and effort, is very high compared to the benefits; the morphological and dimensional information that can be obtained with this technology is limited by restrictions similar to those discussed for Chawla's work. Additionally, the period required to obtain one image at the dozens of micrometers scale may be very long or not possible to obtain and, if not properly carried, curtaining effects during milling may be a drawback (Table 3). Other techniques have similar limitations.

Tomographic analysis by X-rays is limited to the range of tens of micrometers and its resolution is insufficient to reconstruct, with high fidelity, even the texture of the corrosion walls of a specimen attacked by corrosion (Freire-Gormaly, M., MacLean, H., Bazylak, A. 2012 "Microct investigations and pore network reconstructions of limestone and carbonate-based rocks for deep geologic carbon sequestration." Proceedings of the 6th International Conference on Energy Sustainability Conference, ASME2013, July 23-24, San Diego, Calif., USA; Chawla, N., Williams, J. J., Deng, X., McClimon, C., 2009 "Three Dimensional (3D) Characterization and Modeling of Porosity in Powder Metallurgy (P/M) Steels." International Journal of Powder Metallurgy. 45(2)).

Furthermore, in the case of controlled conditions such as those where corrosion coupons and biocoupons are used, a more precise, economic and rapid determination of the corrosion's advance is possible using the technique outlined in this invention, compared to the techniques based on laser and ultrasound signals.

The aforementioned technologies used for morphological and morphometric characterization of pitting corrosion with corrosion coupons and microbiological induced corrosion with biocoupons, based on various microscopy methods, known by the patent applicants are surpassed by the present invention. None of the cited references integrally relates with a procedure for three dimensional morphological characterization of micro-y nano-cavities by SEM and the quantitative determination of the effective corrosion of metallic specimens.

It is therefore an objective of the current invention to provide of a new technique for the three dimensional morphological and morphometric characterization of micro- and nano-cavities caused by pitting corrosion on corrosion coupons and biocoupons. The technique is based on acquiring a polymer mold of these cavities inside a device called "Constant-volume Injection Chamber" (CIVC). The resin employed can be polyacrylic, polystyrenic, polyvinyl o epoxy. The foregoing includes determining the shape, dimensions and distribution of the net of cavities produced by chemical and/or microbiological induced corrosion, applying SEM techniques.

An additional object of the present invention is a procedure to quantitatively determine the effective corrosion of metallic specimens, derived from their volumetric and gravimetric properties in controlled volume and temperature conditions.

The aforementioned objectives and other objectives of the present invention will be more detailed and clearly stablished in the following chapters.

BIBLIOGRAPHY (1) Vaidya, R, U., Hill, M. A. Hawley, M., Butt, D. P. (1998) "Effect of Pitting Corrosion in NaCl Solutions on the Statistics of Fracture of Beryllium." Metallurgical and Materila Transactions A. 29A. November. 2753-2760.
(2) Fraser, H. L., Mills, M. J., Buchheit, R. G., Wang, Y., Ghosh, S., Williams, J. C., Frankel, G. S. Rollett, A. D. Grandt, A. F. (2008) "accelerated metals development by Computation" Air Force Research Laboratory Materials and Manufacturing Directorate Wright-Patterson Air Force Base, OH 45433-7750 Air Force Materiel Command United States Air Force. Report AFRL-RX-WP-TR-2008-4176.
(3) Romero, D., J. (2003) "Corrosion microbiana aerobia en el interior de acueductos de la industria petrolera." Doctorate Thesis. Facultad de Química, Universidad Nacional Autonoma de México. México.
(4) Halvarsson, M., Tang, J. E., Asteman, H., Svensson, J.-E., Johansson, L.-G. 2006 "Microstructural investigation of the breakdown of the protective oxide scale on a 304 steel in the presence of oxygen and water vapour at 600° C." Corrosion Science 48: 2014-2035.

(5) "In situ electrochemical SPM for energy and corrosion studies" American Laboratory, 17. August 2013.

BRIEF DESCRIPTION OF THE INVENTION DRAWINGS

FIG. 1. Surface corrosion micrograph

FIG. 2. Surface corrosion micrograph with phase identification and microstructure.

FIG. 3. Identification and concentration of elements.

FIG. 4. Observation of the pitting corrosion spread, by tilting the stage, at the specimen edge.

FIG. 5. Observation of the pitting corrosion morphology by physically sectioning the specimen.

FIG. 6. Observation of pitting corrosion morphology by sectioning the observation area with an ion beam.

FIG. 7. Observation of the interface of corrosion products on steel in an ion-beam sectioned area.

FIG. 8. Spatial characterization of elements existing at the pitting corrosion zone FIG. 9. In situ topographic characterization of different materials before and after being attacked by corrosion.

FIG. 10. Schematic illustration of the parameters: Effective advance of the corrosion (AEC), true length of the corrosion (LRC), equivalent diameter of the cavity (DEC)

$$\left(DEC = \sqrt{\frac{4A}{\pi}}\right),$$

and the corrosion vector in a stainless steel specimen.

FIG. 11. Schematic illustration of the placement of corrosion specimens and their relative orientation.

FIG. 12. Schematic illustration of a Teflon protector.

FIG. 13. Schematic illustration of the location of the Teflon protector, the coupon and their together assembling.

FIG. 14. Schematic illustration of the Constant-volume Injection Chamber (CIVC) with corrosion coupon.

FIG. 15. Schematic illustration of the Constant-volume Injection Chamber (CIVC) with a bio-coupon.

FIG. 16. Schematic illustration of the Constant-volume Injection Chamber (CIVC) with polymer injected into the coupon.

FIG. 17. Schematic of the polymer and coupon together.

FIG. 18. Schematic of the polymer and coupon illustrating the polymer inside the cavities caused by corrosion.

FIG. 19. Steel coupon during the dilution process.

FIG. 20. Polymer mold of cavities.

FIG. 21. Mold on a SEM specimen holder.

FIG. 22. Device for gold sputtering.

FIG. 23. Specimen mounted on a SEM sample holder and covered with a gold thin film.

FIG. 24. Corrosion coupon after being subjected to pitting corrosion and radial sector of this coupon in cylindrical coordinates.

FIG. 25. Polar rectangle (R) divided into differential polar subrectangles and, center of the polar subrectangle Rij.

FIG. 26. Schematic of a radial section of a coupon, from r=a to r=b and an associated differential polar element.

FIG. 27. Schematic of a differential polar element of steel attacked by corrosion. The grey section is the remaining steel after the attack.

FIGS. 28 and 29. Micrographs show the true morphology of the voids caused by pit corrosion. The images were captured with the electron beam perpendicular to the specimen plane.

FIGS. 30 and 31. Micrographs show the true morphology of the voids caused by pit corrosion. The images were captured with the electron beam tilted 35 degrees with respect to the specimen plane.

FIGS. 32 through 35. Micrographs show textural properties of the steel walls attacked by corrosion.

FIGS. 36 through 39. Micrographs show measurements made on diameters, lengths and spread angles of cavities caused by corrosion.

FIGS. 40 through 42. High-resolution micrographs provide relevant information on the direction the corrosion pitting is advancing in the space of three dimensions.

FIG. 43. Schematic illustration from both, the laser and ultrasound depth reach at the pits crated by corrosion phenomena.

FIG. 44. Corrosion coupon before being exposed to corrosion.

FIG. 45. Picture of the corrosion coupon No. 751 after being attacked by a corrosive liquid flow.

FIGS. 46 through 48. X-ray diffraction analysis results of the corrosion byproducts.

FIG. 49. Coupon after being attacked by corrosive liquid flow and before being cleaned.

FIG. 50. Coupon after being attacked by corrosive liquid flow and cleaned.

FIG. 51. Conventional high-resolution microscopy pictures of the coupon, showing surface features.

FIG. 52. Polymer replica of coupon No. 751.

FIG. 53. Gold sputtered polymer replica of coupon No. 751, showing corrosion pits to be analyzed with SEM.

FIG. 54. Micrographs of the corrosion cavities obtained with the methodology of the present invention for Example No. 5.

FIG. 55. Micrograph of a corrosion cavity captured with the electron beam perpendicular to the coupon plane (Elevation view, 0°).

FIG. 56. Micrograph of a corrosion cavity captured with the electron beam tilted 52° with respect to the coupon plane.

FIG. 57. Micrograph showing a flat corrosion region surrounding a pit.

FIGS. 58 and 59. Plots showing histograms of both, the pits and flat-corrosion depth distributions respectively.

FIG. 60. Micrograph showing corrosion cavities produced by the corrosion attack on the coupon, in the space of three dimensions, corresponding to the sixth section of the graphic interface in this invention.

DETAILED DESCRIPTION OF THE INVENTION

The present invention refers to a procedure:

a) To Determine the three dimensional morphology of micro and nanocavities produced by chemical and/or microbiological corrosion in metallic materials, along with the effective advance of the corrosion, the true length of the corrosion cavities and their associated parameters (FIG. 10): vector field of corrosion, intensity of corrosion and the diameter/true-length ratio of corrosion, applying SEM techniques and analytic, volumetric and gravimetric formulations; FIG. 10 illustrates the parameters: Effective advance of corrosion (AEC), true length of corrosion (LRC), surface-cavity equivalent diameter (DEC)

$$\left(DEC = \sqrt{\frac{4A}{\Pi}}\right)$$

and corrosion vector in a metallic specimen.

b) To quantitatively determine the rate of chemical and/or microbiological corrosion in metallic materials based on their volumetric and gravimetric properties; and
c) To obtain a user friendly interface to access numeric information and micrographs describing the output of the above determinations.

Specifically, the current invention is related to the laboratory procedures, analytic expressions, devices, processes and calculations required to characterize micro and nano-cavities caused by chemical and/or microbiological pitting corrosion in coupons and biocoupons.

The procedure of the present invention is restricted to equipment or elements made of metallic materials prone to be attacked by corrosion, which may be diluted in a hydrochloric acid environment (HCl).

The procedure of the present invention includes the following steps:

1. Reference marks for orientation and weight determination. Whenever possible, it is recommended to place marks on the specimen in order to orientate it with respect to the medium in which the corrosion occurs. This will allow establishing the position of the corrosion vectors field, if it exists, with respect to the medium (FIG. 11), when the corrosion micrographs are analysed. This may be useful if the environment is fluid flowing inside a pipe. Then the specimen weight is determined. FIG. 11 illustrates the relative position of corrosion coupons and their relative orientation.
2. Metallic coupons preparation. This preparation includes dimensions measurement and weighing. In addition, Teflon protectors will partially cover metallic coupons so that these may be attacked on the exposed surface. These protections eventually will help to accurately integrate the specimen-attacked volume. FIG. 12 presents a schematic of the Teflon cover and FIG. 13 shows a specimen of the said protector positioned on the coupon.
3. Corrosion testing or attacking. The biocoupon or corrosion coupon and Teflon cover are installed in the equipment or metallic element to be monitored, then the corrosion test is carried, if possible exposing only one surface of the specimen to the corrosive environment (FIG. 13).
4. Specimen cleaning and drying. After being corrosively attacked, and to accurately observe texture details and measure characteristic distances within the cavities, it is required that the coupon may be free of corrosion by-products and other substances as well as completely dry. The specification for this cleaning can be found in the standards, provided by PEMEX, NRF-194-PE-MEX-2007 and NRF-005-PEMEX-2009 or by other institutions, such as ASTM G1-90 (reapproved 1999), or NACE Standard RP0775-2005 as specified.
5. Obtaining a replica of the corrosion cavities. To obtain a replica of the corrosion cavities, these are penetrated, under high vacuum pressure, by a polymer, which is placed in a vacuum chamber along with the coupon; after the catalytic reaction is completed, the metal coupon is dissolved leaving behind a high fidelity copy of the said cavities. The remnant is a three dimensional mold of these cavities.
    5.1 Insertion of the specimen into the CIVC. To obtain the mold of the corrosion cavities the coupon is inserted into the chamber called the "Controlled-Volume Injection Chamber (CIVC)"; this chamber is titanium or stainless steel made. For this purpose, the base of the chamber is removed and the coupon introduced (FIGS. 14 and 15). In the description that follows, the same process applies for bio-coupons. The CIVC includes lower and upper caps, and two valves or gates in the upper cap. The largest valve (C1) allows to pour fluids into the the CIVC and the shortest (C2) allows to both, vent gases and liquids out of the CIVC and observe when the chamber is completely filled.

FIGS. 14 and 15 show schematics of the CIVC with a coupon and biocoupon inside respectively, were: C1 and C2 are the valves or gates on the CIVC for the fluids flow, and $V_{CA}$ is the known volume inside the CIVC.

5.2 Polymer injection. Once the attacked coupon is inserted, the complete system (CIVC and coupon) is installed inside a high vacuum chamber, which is hermetically sealed and then subject to vacuum pressure. Inside this chamber, the polymer fills into the CIVC; Valve C2 permits to know when the chamber is full (FIG. 16).

FIG. 16 shows a schematic view of the CIVC and the polymer impregnating the coupon.

The polymer used is mainly an acrylic, styrene, vinyl or epoxy type of resin.

The density of the resin used is determined ($\rho_r$).

This step finishes when the resin used polymerizes.

5.3 Extraction of the specimen from the CIVC. The coupon and polymer are extracted from underneath the CIVC, and then it is washed, weighed and prepared for the process of dissolving the metal (FIG. 17 y 18).

FIG. 17 shows a schematic view of the polymer and coupon together, while

FIG. 18 shows a schematic view of the coupon and the polymer inside the pitting cavities, where:
    $V_{TR}$ the resin total volume;
    $V_1$ y $V_2$ the known volumes of valves C1 and C2, respectively;
    $V_{CR}$ is the attacked volume of Steel; and
    $V_{REA}$ is the metal remaining volume.

5.4 Dissolution of the specimen. The polymer-injected steel coupon to be dissolved is placed into a precipitation glass and submerged in concentrated hydrochloric acid (HCl), (FIG. 19).

FIG. 19 shows a metallic coupon during dissolution.

The result of this process is the volume, in resin, of the CIVC control chamber plus the volume of the metal already attacked (Grayest section in FIGS. 17 and 18).

6. Washing and drying of the corrosion-cavities replica. What remains, once the metal coupon has been dissolved, is the three dimensional replica of the corrosion cavities, impregnated with residues of hydrochloric acid. It must be cleaned to eliminate said acids and whatever solid residue remains. The washing is performed as follows:

Place the replica into a Petri dish.

Gently drip ionized water onto the replica to minimize the risk of damage to the fragile polymer copy of the cavity structure.

After the specimen has been carefully washed, it is placed into a desiccator for at least a day to ensure there are no remaining drops or thin films of water.

The final output is the morphology of the cavities caused by corrosion represented in a polymer mold as illustrated in FIG. 20.

7. Mounting the mold on a SEM sample holder. The resin mold is attached to an aluminum SEM sample holder or stub, with doubled sided carbon tape as illustrated in FIG. 21. This sample holder permits to handle the sample and introduce it into the scanning electron microscope.

FIG. 21 Shows the mounting of the resin mold on the SEM sample holder.

8. Gold sputtering of the resin mold. In this step. The specimen already contains a polymer replica of the structure of the cavities caused by corrosion. In order to study details of this structure by SEM, it is necessary to coat it with a thin film of electron conductive material such as carbon, gold or gold-palladium (FIGS. 22 and 23).

FIG. 22 Shows the gold sputtering device and FIG. 23 shows the replica already covered with a thin film of gold and installed on a SEM sample holder.

9. Observation by Scanning Electron Microscopy (SEM). Once it is coated, the resin replica is ready to be introduced into a SEM vacuum chamber to determine the shapes of, measure the dimensions of and identify the cavities of the sample as well as any trend in their orientation within the steel coupon. More micrographs of pitting corrosion cavities examples, as obtained by SEM, will be presented in further sections.

10. Obtention of the amount of attacked metal and volumes calculation. FIG. 24 helps to explain how the determination of the amount of attacked metal and volumes calculation are made. This figure shows s schematic of a corrosion coupon after being attacked by pitting corrosion; it also shows a radial sector of the coupon inside a polar coordinate system.

Let R be a region in polar coordinates, defined by:

$$T=\{(r,\theta,z) | a \leq r \leq b;\ 0 \leq \theta \leq 2\pi;\ 0 \leq Z \leq t\} \quad (1)$$

Subdividing R into a mesh of elements (differential elements), such that a differential element of this region is $R_{ij}$ (center of the differential element) as shown in FIG. 25.

FIG. 25 illustrates a schematic drawing of a polar rectangle (R) divided into differential elements and the center location of polar element $R_{ij}$.

The volume below the surface of this element will be (FIGS. 26 and 27):

$$\Delta V = f(r_i^c \cdot \cos \theta_j^c, r_i^c \cdot \operatorname{Sen} \theta_j^c) r \Delta r \Delta \theta \quad (2)$$

FIG. 26 shows a schematic drawing of coupon radial section, from the boundaries r=a to r=b, and a polar differential element in it, while FIG. 27 shows a schematic drawing of a polar differential element of steel already attacked by a corrosion process, where the grayest section is the remaining steel.

By integrating over the entire region defined in (1), one obtains:

$$V = \int\int_R f(r,\theta) dA = \lim_{m,n\to\infty} \sum_{i=1}^{m} \sum_{j=1}^{n} f(r_i^c, \theta_j^c) \Delta r \Delta \theta \quad (3)$$

Equation (3) is conceptually exact; it describes correctly the calculation of the volume of steel remaining after the corrosion. An equivalent equation can be written in integral form as:

$$V = \int_\alpha^\beta \int_a^b f(r \cdot \cos \theta, r \cdot \operatorname{Sen} \theta) r\, dr\, d\theta \quad (4)$$

The biocoupon and corrosion coupons have the integration limits presented in Table 4.

TABLE 4

Integration limits of equation (4) for corrosion coupons and biocoupons.

| Coupon | α | β | a | b |
|---|---|---|---|---|
| Corrosion Coupons | 0 | 2π | a | b |
| Biocoupon | 0 | 2π | 0 | b |

Calculation of the Remaining and Attacked Volumes:

As one of the contributions to the present invention it was designed an experimental apparatus, shown illustratively on FIGS. 14 and 15, called "Constant-Volume Injection Chamber (CIVC)" fabricated in metal, preferably titanium or stainless steel. This device was designed to permit the acquisition of, by use of a control chamber, the volume expressed by equation (4). This is done in the following way:

1. The coupon is preferably placed into a Teflon protector (FIGS. 12 and 13).
2. The coupon or coupon-Teflon protector from the previous step is installed into a pipe, preferably exposing just one side of the coupon to the effects of corrosion (FIG. 13).
3. After the corrosion test or corrosive attack, the coupon must be free of corrosion byproducts and other substances, and also completely dry so that texture and size of cavities caused by the corrosion phenomena may be accurately observed.
4. Upon completion of the cleaning and drying of the attacked coupon, it is placed into the CIVC by removing the base of the chamber and inserting the coupon in it. This chamber has two gates available on its upper part; the larger one (C1) permits fluids to be poured into the chamber while the smaller (C2) allows, at the same time: venting of the air, capture the overflow within the CIVC, and to determine when the CIVC is full (FIGS. 14 and 15).
5. Under vacuum pressure conditions, a resin is poured into the CIVC until it is full and then the resin polymerizes.
6. Once the CIVC is full, the lid of the chamber is turned 30° (FIG. 16). This establishes a known volume $V_{CA}$ within the chamber (FIGS. 17 and 18). Furthermore, from the fabrication process, the volumes $V_1$ and $V_2$ of valves $C_1$ and $C_2$ are also known.
7. The density, $\rho_r$, of the resin is determined.
8. Once the resin polymerizes, the attacked coupon and resin are extracted together and the steel component is dissolved in hydrochloric acid (HCl).
9. The result of the dissolving process is the volume, in resin, of the control chamber plus the volume within the coupon caused by pitting in this element (FIGS. 17 and 18).
10. The element obtained in step (9) is inverted and gold-coated, then it is ready to be analyzed by SEM. It consists of a high fidelity copy of the morphology of the corrosion within the steel coupon (Grayest section in FIGS. 17 and 18).

In it one can observe:
a. The shape of the corrosion,
b. Maximum sizes of the corrosion (by changing the observation angle within the SEM vacuum chamber);
c. Orientation of the corrosion cavities, if it exists (Idem),
d. True length of the corrosion,
e. Effective advance of the corrosion.

11. As an added value, the volume of the corrosion can be calculated by use of the following equation:

$$V_{TR} = V_{CA} + V_1 + V_2 + \left( \int_0^{2\pi} \int_a^b f_1(r\cos\theta, r\sin\theta) r \, dr \, d\theta - \lim_{m,n\to\infty} \sum_{i=1}^m \sum_{j=1}^n f_2(r_i^c \cdot \cos\theta_j^c, r_i^c \cdot \sin\theta_j^c) r_i^c \Delta A_i \right) \quad (5)$$

Where:

$V_{TR}$ is the resin total volume;

$V_{CA}$ is the know volume within the CIVC;

$V_1$ and $V_2$ are the know volumes of gates $C_1$ and $C_2$ respectively;

$f_1$ is the volume function of the coupon before the corrosive attack and, $f_2$ is the corresponding volume after the attack.

The value within the parenthesis is the volume of steel attacked ($V_{CR}$) where:

$$V_{CR} = \left( \int_0^{2\pi} \int_a^b f_1(r\cos\theta, r\sin\theta) r \, dr \, d\theta - \lim_{m,n\to\infty} \sum_{i=1}^m \sum_{j=1}^n f_2(r_i^c \cdot \cos\theta_j^c, r_i^c \cdot \sin\theta_j^c) r_i^c \Delta A_i \right) = \quad (6a)$$

$$V_{TR} - (V_1 + V_2 + V_{CA})$$

which can also be expressed as:

$$V_{CR} = V_{TR} - (V_1 + V_2 + V_{CA}) \quad (6b)$$

Equation (6b) permits the calculation of the attacked volume of steel knowing the control chamber volume ($V_{SA}$), the resin entrance ($V_1$) and exit ($V_2$) valves volumes, and the total volume and density of resin used ($V_{TR}$), and ($\rho_r$) respectively.

Finally, the present invention also provides a graphic interface to interact and to access the information of data, and volumetric and gravimetric calculations of coupons and/or biocoupons before and after being attacked by corrosion environments, it also includes micrographs depicting the attack.

The graphic interface in the present invention includes six sections:

A first section contains information of coupons or biocoupons before being attacked;

A second section contains information of coupons or biocoupons after being attacked;

A third section shows the results of volumetric and gravimetric numeric calculations of coupons or biocoupons before and after being attacked;

A fourth section where, by a sampling process, the depths of corrosion pits and uniform corrosion statistical distribution are determined. This is achieved using the information obtained in the sections above, and the morphologic and morphometric characterization based on optic and scanning electronic microscopy (MEB) works.

A fifth section where de maximum depth of penetration of corrosion is determined according to NACE SP0777-2013 Item No. 21017 recommendation, through a sampling process and using the information obtained from the sections above.

A sixth section illustrates, through micrographs, the corrosive attack on the coupon or biocoupon.

EXAMPLES

In order to have a better understanding of this invention, and without limiting its scope, the following section presents some practical examples.

The micrographs interpretation is as follows:

What is observed as solid are the empty spaces or cavities already visible; and

What is observed as empty places are the spaces originally occupied by the metal, visible no more.

Example 1. Surface Morphology Characterization of the Areas Affected by Pitting Corrosion in a Steel Coupon From the application of the present invention methodology to a steel corrosion coupon, exposed to a corrosive multiphase-fluid in a high velocity flow and high-pressure regime, the following micrographs of the shape and distribution of cavities corresponding to pitting corrosion were obtained.

It is worthy to underline that the observation angle selected between the specimen plane and the optical axis of the microscope is very important to observe the morphologic characteristics of cavities produced by the corrosion.

FIGS. 28 and 29 correspond to SEM micrographs obtained with the electron beam perpendicular to the plane of the specimen, in two different regions, as is indicated on the same micrographs.

FIGS. 30 and 31 correspond to SEM micrographs obtained in two different regions of the specimen, with the stage where the sample is supported tilted 35 degrees with respect to the horizontal, as indicated in the right-hand side illustration in the same figures.

The following conclusions can be drawn from this example:

1. The procedures of the present invention allow to obtain scanning electron microscopy (SEM) images of the corrosion cavities or corrosion pits in a tree-dimensions space, whereas the conventional SEM images of pitting corrosion deliver information in two dimensions, providing a rough idea of their depth, as shown in FIG. 1.
2. The images of FIGS. 28 through 31, obtained by the procedures of the present invention, present the true morphology and complexity of the spaces created by the corrosion process, as opposed to the limited information of depth provided by the SEM surficial images.
3. Applying the procedures of the present invention, the cavities created by the corrosion process are obtained as three dimensional objects; thus by manipulating the SEM stage in rotation and tilting, it is possible to observe those cavities at any angle, which in this example are stalactites-like.
4. The statistical distribution of depths and surface diameters of the pits is not enough to describe the reach of the corrosion damage, This can only be achieved by determining the shape and depth of the corrosion pits as observed in FIGS. 28 through 31, obtained by means of the present invention.

Example 2. Corrosion-Pitting Inside Walls-Texture Characterization in a Steel Corrosion Coupon The same specimen from Example 1, exposed to a corrosive multiphase-fluid in a high-velocity flow and high-pressure regime, provided the following micrographs of the cavities-walls texture, corresponding to pitting corrosion.

FIGS. 32 through 35 present micrographs showing typical patterns of corrosion development, and allow observing the unique cavities growth textures on the cavities left by the corrosion in the steel specimen.

Example 3. Measurement of Equivalent Diameters and Depths of Voids Left by Pitting Corrosion in a Steel Corrosion Coupon The same specimen from Example 1, exposed to a corrosive multiphase-fluid in a high-velocity flow and high-pressure regime, provided the following micrographs, which allowed to measure the equivalent diameters and depths of the voids left by pitting corrosion.

FIGS. 36 through 39 present micrographs showing measurements of diameters, depths and advancing corrosion-growth angles on the cavities left by the corrosion in the steel specimen.

Example 4. Identification of Preferential Corrosion Pitting Growth Directions in Steel Coupons High-resolution micrographs shown in FIGS. 40 through 42, obtained by appropriate manipulation of the SEM stage angles, permit to acquire valuable information of the direction, in three dimensions, of the growth of corrosion cavities. FIG. 43 illustrates schematically both, the depth of reach of ultrasound and laser sensors and the corrosion pits. FIG. 43 along with FIGS. 40 through 42, shows that this invention allows, as opposed to ultrasound and laser devices:

To identify the true advance of corrosion with respect to the non-attacked thickness of the corrosion coupon, also called "Effective advance of corrosion" (AEC);
To determine the "True length of corrosion cavities" (LRC); and
To determine the unit vectors corresponding to the dominant directions of corrosion cavities, If they exist.

Example 5. Industrial Application of the Present Invention

Initial Information:

For this application it was used a corrosion coupon with identification number 751, which is illustrated in FIG. 44 and whose geometrical and weight data is presented on Table No. 5.

Saline chamber description. The functional configuration of this chamber was developed following the ASTM TM0169/G31-12a recommendations: item No. 6. Apparatus, 7. sampling y 8. Test specimen. The chamber includes:

An Akua-Kal water heather with a thermostat and temperature control in the range of 50° C. to 40° C. and 5° C. sensitivity,
A Delter air-compressor with diffusor and maximum pressure of 5 psi,
A thermometer to monitor temperature in the range 0° C. to 300° C. and 5° C. sensitivity, and
An acrylic-made frame to install and support in place the corrosion coupons during the corrosive attack inside the saline chamber.

The corrosion coupon, after being attacked by the corrosive flow, is depicted in FIG. 45.

Corrosion Products Analysis

Chemical analyses of the coupon surficial corrosion products, made by X-rays energy dispersive spectrometry (EDS) in a Jeol 35CF SEM, exhibit two main phases: the first one shows an intense yellow color and the other dark brown color.

According to the existing elements, the balance equation in the corrosion process provides:

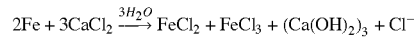

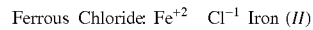

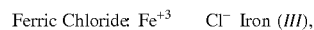

and Calcium hydroxide

Chemical analyses performed in a Jeol 35CF SEM confirmed that the elements existing in the corrosion products coincide with the above equation.

Two Iron oxidation states were found with X-ray diffraction analysis. This allows affirming that the bubbling corrosion attack method properly provided oxygen, so that the two oxide species were formed. Also, additional compounds, formed during the same reaction, were detected; Calcium hydroxide and Chlorine compounds. Results of these analyses are presented in FIGS. 46, 47 and 48.

Cleaning and Surface Details of Areas Attacked by the Corrosive Flow:

Cleaning of the attacked coupon was done following ASTM recommendation, ASTM G1-03 (reaproved in 2011)

TABLE No. 5

Geometrical and weight data of corrosion coupon No. 751.

| Coupon No. | Weight, before corrosive attack (gr) | Average thikness (mm) | Average diameter (mm) | Saline chamber temperature (° C.) | Exposure time (days) | Weight, after corrosive attack (gr) |
|---|---|---|---|---|---|---|
| 751 | 17.3033 | 3.005 | 31.601 | 35 | 170 (4,080 hrs.) | 16.4725 |

Coupon No. 751 Corrosion Exposure Setting:

This coupon was exposed to a corrosive two-phase flow in a saline chamber where the liquid phase was 8% concentration Calcium chloride (CaCl2) in 35° C. temperature distilled water and the gaseous phase was air bubbles, for a 4,080.0 hours period.

Standard Practice for Preparing, Cleaning, and Evaluating Test Specimens. FIG. 49 shows the attacked coupon before cleaning and FIG. 50 the same coupon after cleaning.

Conventional microscopy images of the coupon surface show the topographic details presented in FIG. 51. However they did not allowed observing the true morphology of corrosion cavities, neither their depth nor their advance could be completely determined by this microscopy technique or by laser or ultrasound based techniques.

This Methodology Application Results:

The procedures of the present invention, applied to the coupon, allowed to obtain a polymeric replica, as presented in the picture of FIG. 52.

Finally, a polymeric replica of the corrosion cavities was obtained, as it is depicted in FIG. 53, already covered with a 30 nm Gold thin film, in order to be studied with scanning electron microscopy.

Morphology

FIG. 54 presents SEM micrographs of cavities for this example, obtained with the procedures of this invention.

It is important to underlain that the procedure of the present invention allows to clearly observe the differences between shape and texture in the corrosion pits, when coupons fabricated with the same material (such as the ones presented in examples 2 and 5, which is SAE 1018 steel), are subjected to different corrosive environments and conditions. FIGS. 34 and 35 from Example 2 show the forms and texture of corrosion cavities when the specimen was exposed to a high pressure and high velocity corrosion flow in a multiphase corrosion environment: These conditions are different to those shown in FIG. 54 from Example 5, where the coupon was exposed to corrosion in a saline chamber. FIG. 55 shows a corrosion cavity observed in an angle perpendicular to the specimen plane (elevation view, 0°), and FIG. 56 shows the same cavity rotated 52°, evidencing the advantage and relevance of having the cavities in three dimensions.

Corrosion Rate

Corrosion rate measurement was performed according to both, ASTM G1-03 (2011), and NACE SP0775-2013 Item 21017.

Table No. 6 along with FIG. 44 shows the corresponding results.

TABLE No. 6

Corrosion rate calculation, according to ASTM G1-03 (2011) ($V_C$), and NACE SP0775-2013 Item 21017 (CR)

| Initial weight | 17.3 | gr |
|---|---|---|
| Final weight | 16.47 | gr |
| W | 0.83 | gr |
| Thickness (t) | 0.3 | cm |
| D | 3.16 | cm |
| di1 | 0.82 | cm |
| di2 | 1.32 | cm |
| A | 6.46 | cm² |
| T | 4080 | Hours |
| Vt | 2.08 | cm³ |
| ρ | 8.31901556 | gr/cm³ |
| K | 87600 | mm/year |
| K | 3450000 | mils/year |

Corrosion rate ($V_C$) calculation according to ASTM G1-03 (2011):
Corrosion rate, $v_C = (KW)/(A\,T\,D)$

| $v_C$ | 0.33 | mm/year |
|---|---|---|
| $v_C$ | 13.06 | mils/year |

TABLE No. 6-continued

Corrosion rate (CR) calculation according to NACE SP0775-2013 Item 21017

| A | 646.72 | mm² |
|---|---|---|
| T | 170 | days |
| ρ | 8.31901556 | gr/cm³ |
| W | 0.8308 | gr |
| K | 1 | mm/year |

$CR = (W \times 365 \times 1000)/ATDK$

| CR | 0.33 | mm/year | where:
A Corrosion coupon exposed area,
T Time of corrosion exposure,
W Weight lost due to corrosion exposure equal to weights difference: initial − final,
Vt Specimen total volume, before corrosion attack,
ρ Specimen density,
K Constant that accounts for units consistency, and
$V_C$ and CR are the corrosion rates in the indicated units.

The calculation results presented in Table No. 6, allow concluding that the corrosion rate is severe, according to Table 2 of the NACE SP0775-2013 corrosion severity criteria.

The rate of corrosion applying the procedures of this invention is presented in Table No. 7.

Is it can be observed, the results for the corrosion rate according to the ASTM G1-03 (2011), and NACE SP0775-2013 Item 21017 recommendations (Table No. 6) match each other, providing a corrosion rate of 0.33 mm/year, while the expression used in the present invention, 0.3453 (Table No. 7) is slightly off, this is due to the fact that weight determinations for corrosion rate are more accurate than the corresponding determinations in volume.

This confirms both, this methodology reliability and the expression used in the present invention.

TABLE No. 7

Corrosion rate calculation using the CIVC, According to the procedures in the present invention.
$V_{RC} = V_{TR} - (V_1 + V_2 + V_{CA})$

| $V_{TR}$ = Polymer total volume | $m_{TR}/\rho_R$ |
|---|---|
| $m_{TR}$ = Polymer total mass = | 10.87 g |
| $\rho_R$ = Polymer density = | 1.234 g/cm³ |
| $V_{CA}$ = Total volume of the CIVC = | 8182.7 mm³ |
| $V_1$ = C1 gate volume = | 254.77 mm3 |
| $V_2$ = C2 gate volume = | 266.94 mm³ |
| $V_{RC}$ = Attacked steel volume = | 103.96 mm³ |
| A = Specimen exposed área = | 646.47 mm² |
| The thickness for 170 days will be: | |
| $h_{170} = V_{RC}/A =$ | 0.1608 mm |
| Therefore, the corrosion rate, corresponding to a thickness for 365 days (a year) will be: | |
| VC = $h_{365}$ = | 0.3453 mm/year |

Morphometry

Depth of pits due to corrosion was obtained by randomly sampling 42 cavities, using the CIVC geometry and attending to the following relevant considerations: There were two stages observed during the corrosion attack, the first stage is characterized by a uniform corrosive deterioration of the specimen, where flat regions are observed (FIG. 57, surrounding the pit), and a second stage where the pitting is observed; Table No. 8 shows the depth measurement results for both stages, such that the sum of them provides the total depth of corrosion attack.

TABLE No. 8

Measurements of depth of corrosion attack.

| Cavities (mm) | Uniform corrosion (mm) |
|---|---|
| 1.281 | 0.77 |
| 1.089 | 0.73 |
| 0.953 | 0.88 |
| 0.422 | 0.22 |
| 1.192 | 0.73 |
| 1.307 | 0.97 |
| 1.14 | 0.87 |
| 1.127 | 0.79 |
| 0.948 | 0.73 |
| 0.884 | 0.61 |
| 0.731 | 0.38 |
| 0.447 | 0 |
| 0.127 | 0 |
| 0 | 0 |
| 0.178 | 0 |
| 0 | 0 |
| 0 | 0 |
| 0.653 | 0.28 |
| 0.653 | 0.38 |
| 0.961 | 0.59 |
| 0.98 | 0.71 |
| 1.448 | 1.09 |
| 1.435 | 1.12 |
| 0.633 | 0.33 |
| 0.576 | 0.33 |
| 0.64 | 0.28 |
| 0.704 | 0.47 |
| 0.896 | 0.49 |
| 0.928 | 0.55 |
| 0.999 | 0.59 |
| 1.115 | 0.78 |
| 1.204 | 0.9 |
| 1.243 | 0.88 |
| 1.153 | 0.97 |
| 1.461 | 1.04 |
| 1.348 | 1.19 |
| 1.243 | 1.07 |
| 0.948 | 0.54 |
| 0.946 | 0.74 |
| 0.637 | 0.45 |
| 0.651 | 0.49 |
| 0.609 | 0.25 |
| Max = 1.461 | 1.192 mm |

Plots were obtained with these sets of data and are presented in FIGS. 58 and 59

Plots in FIGS. 58 and 59 present both, the distribution of depths due to pitting corrosion and uniform corrosion respectively, for the indicated intervals in a sample of size 42.

Measurements made, by applying the procedures of the present experiment, indicate that maximum depth of pitting reached half of the original non-attacked coupon thickness, which is consistent and confirms the "severity" level determined by NACE criteria, in this example.

Maximum Corrosion Rate

By the use of Table No. 8 data set, it was determined the maximum depth of corrosion cavities in a measurement depth sampling of size 42; this, along with the exposure time, allowed to calculate the maximum corrosion rate following the NACE SP0777-2013 Item No. 21017 recommendation, as shown in Table No. 9.

TABLE No. 9

Maximum corrosion rate determination according to NACE SP0777-2013 Item No. 21017.

Maximum corrosion rate determination according to NACE SP0777-2013 Item No. 21017
PR = Deepest cavity value (mm) × 365/Exposure time (days) (m/y)
Uniform corrosion value = 1.04 mm
Corrosion cavity value = 0.42 mm
Deepest cavity value = 1.46 mm
Exposure time = 170 days
PR = (1.461 × 365)/170 = 3.14 mm/year

Example No. 6

Graphic interface to interact and to access the coupon data, its volumetric and gravimetric calculations, before and after being attacked by a corrosion process, and a micrograph illustrating a result of such attack.

To illustrate the operation if this interface, the information and results from example 5 corresponding to a corrosion coupon number 751 were used, where the procedures of the present invention were applied.

Initial data of the corrosion coupon, before being attacked by corrosion, included in the first information section are the following:

Corrosion coupon number: 751
  Geometric Data:
External diameter (De): 3.1601 cm
Thickness (t): 0.3005 cm
Shortest internal diameter ($di_1$): 0.822 cm
Largest internal diameter ($di_2$): 1.3248 cm
  Gravimetric Data:
Initial weight (W): 17.3033 g Final data of the corrosion coupon, after being attacked by corrosion, included in the second information section are the following:

| | |
|---|---|
| Final weight ($W_f$) | 16.47 gr |
| Corrosive environment exposure time (T) | 4,080.0 Hrs |

Results of coupon number 751 volumetric and gravimetric calculations before and after being attacked, corresponding to the third section were the following:

| | |
|---|---|
| Loss of weight = difference in weight: initial − final, (W) | 0.83 gr |
| Area exposed to corrosion (A) | 6.46 cm² |
| Coupon Total volume, before corrosion exposure, ($V_t$) | 2.08 cm³ |
| Density (D) | 8.31901556 gr/cm³ |

Rate of corrosion ($V_c$) calculation, according to ASTM G1-03 (2011):

$$v_c = (KW)/(A\,T\,D)$$

Where:
K=87600.00 mm/year
K=3450000.00 mils/year

| | | |
|---|---|---|
| $v_C$ | 0.33 | mm/year |
| $v_C$ | 13.06 | mils/year |

Rate of corrosion (CR) calculation, according to NACE SP0775-2013 Item 21017:

$$V_{RC} = V_{TR} - (V_1 + V_2 + V_{CA})$$

Where:

| | | |
|---|---|---|
| A | 646.72 | mm² |
| T | 170 | days |
| K | 1 | mm/year |
| CR | 0.33 | mm/year |

Corrosion rate calculation using the CIVC,
According to the procedures in the present invention.

$$V_{RC} = V_{TR} - (V_1 + V_2 + V_{CA})$$

| | |
|---|---|
| $V_{TR}$ = Polymer total volume | $m_{TR}/\rho_R$ |
| $m_{TR}$ = Polymer total mass = | 10.87 g |
| $\rho_R$ = Polymer density = | 1.234 g/cm³ |
| $V_{CA}$ = Total volume of the CIVC = | 8182.7 mm³ |
| $V_1$ = C1 gate volume = | 254.77 mm3 |
| $V_2$ = C2 gate volume = | 266.94 mm³ |
| $V_{RC}$ = Steel attacked volume = | 103.96 mm³ |
| A = Specimen exposed área = | 646.47 mm² |
| The thickness for 170 days will be: | |
| $h_{170} = V_{RC}/A =$ | 0.1608 mm |
| Therefore, the corrosion rate, corresponding to a thickness for 365 days (a year) will be: | |
| VC = $h_{365}$ = | 0.3453 mm/year |

As can be observed, the results for the corrosion rate according to the ASTM G1-03 (2011), and NACE SP0775-2013 Item 21017 recommendations (Table No. 6) match each other, providing a corrosion rate of 0.33 mm/year, while the expression used in the present invention, 0.3453 (Table No. 7) is slightly off, this is due to the fact that weight determinations for corrosion rate are more accurate than the corresponding determinations in volume.

This confirms both, this methodology reliability and the expression used in the present invention.

The use of information in the sections above, allowed to obtain the statistical distribution of depths of both, the pitting corrosion and uniform corrosion, corresponding to the fourth section in the interface, where the following results were obtained:

| Measurements of depth of corrosion attack. | |
|---|---|
| Cavities (mm) | Uniform corrosion (mm) |
| 1.281 | 0.77 |
| 1.089 | 0.73 |
| 0.953 | 0.88 |
| 0.422 | 0.22 |
| 1.192 | 0.73 |
| 1.307 | 0.97 |
| 1.14 | 0.87 |
| 1.127 | 0.79 |
| 0.948 | 0.73 |
| 0.884 | 0.61 |
| 0.731 | 0.38 |
| 0.447 | 0 |
| 0.127 | 0 |
| 0 | 0 |
| 0.178 | 0 |
| 0 | 0 |
| 0 | 0 |
| 0.653 | 0.28 |
| 0.653 | 0.38 |
| 0.961 | 0.59 |

| Measurements of depth of corrosion attack. | | |
|---|---|---|
| Cavities (mm) | Uniform corrosion (mm) | |
| 0.98 | 0.71 | |
| 1.448 | 1.09 | |
| 1.435 | 1.12 | |
| 0.633 | 0.33 | |
| 0.576 | 0.33 | |
| 0.64 | 0.28 | |
| 0.704 | 0.47 | |
| 0.896 | 0.49 | |
| 0.928 | 0.55 | |
| 0.999 | 0.59 | |
| 1.115 | 0.78 | |
| 1.204 | 0.9 | |
| 1.243 | 0.88 | |
| 1.153 | 0.97 | |
| 1.461 | 1.04 | |
| 1.348 | 1.19 | |
| 1.243 | 1.07 | |
| 0.948 | 0.54 | |
| 0.946 | 0.74 | |
| 0.637 | 0.45 | |
| 0.651 | 0.49 | |
| 0.609 | 0.25 | |
| Max = | 1.461 | 1.192 mm |

By the use of the information obtained in the sections above, it was determined the maximum depth of corrosion cavities in a measurement depth sampling of size 42; this allowed, along with the exposure time, to calculate the maximum corrosion rate following the NACE SP0777-2013 Item No. 21017 recommendation, corresponding to the fifth section, using the information in the sections above:

Maximum corrosion rate determination according to NACE SP0777-2013 Item No. 21017
PR = Deepest cavity value (mm) × 365/Exposure time (days) (m/y)
Uniform corrosion value = 1.04 mm
Corrosion cavity value = 0.42 mm
Deepest cavity value = 1.46 mm
Exposure time = 170 days
PR = (1.461 × 365)/170 = 3.14 mm/year Finally, FIG. 60 shows one of the many micrographs obtained from corrosion cavities, in three dimensions, which were produced by a corrosive attack to the coupon. This corresponds to the sixth section of the graphic interface developed in the present invention.

The invention claimed is:
1. A method for determining morphology and quantitative growth of a plurality of micro and nanocavities produced by chemical and/or microbiological corrosion in a metallic materials, in the space of three dimensions, comprising the following steps:
   a) Placing reference marks on a metal coupon to orient the metal coupon with respect to a corrosive medium and weighing the metal coupon before step c);
   b) Preparing the metal coupons before step c), including determining physical dimensions of the metal coupon and installing a protector that partially covers the metal coupon;
   c) Exposing the metal coupon to the corrosive medium;
   d) Cleaning the metal coupon, including drying the metal coupon and then weighing the metal coupon;
   e) Obtaining a polymer or resin replica of corrosion cavities of the metal coupon by use of a CIVC in a low pressure environment, extracting the polymer or resin replica from the CIVC, and dissolving the metal coupon such that the polymer or resin replica remains intact;

f) Washing and then drying the polymer or resin replica;

g) Mounting the polymer or resin replica on an SEM sample holder;

h) Coating the polymer or resin replica with a thin film of a an electrically conductive material by sputtering;

i) Obtaining micrographs of the polymer or resin replica with SEM for performing morphologic and/or morphometric analysis; and j) Calculating amount of attacked metal and volume of remaining metal.

2. The method of claim 1, wherein the metal coupon is dissolved in a hydrochloric acid environment.

3. The method of claim 1, wherein the metal coupon is a biocoupons or a corrosimetric coupon.

4. The method of claim 1, wherein the protector is a Teflon protector.

5. The method of claim 1, wherein step c) further comprises first installing the metal coupon and/or the protector in a piece of equipment or an element to be studied in such a way that only one face of the metal coupon is exposed to the corrosive medium.

6. The method of claim 1, wherein step e) further comprises:
  i. Inserting the metal coupon into the CIVC,
  ii. Injecting polymer or resin,
  iii. Extracting the metal coupon from the CIVC,
  iv. Dissolving the metal coupon.

7. The method of claim 6, wherein the CIVC in sub-step i is a control chamber which includes a lower cap and an upper cap and two valves or gates; wherein the larger valve or gate (C1) allows to pour fluids into the CIVC and the smaller valve or gate (C2) allows to both vent gases and liquids out of the CIVC and to observe when the CIVC is completely filled.

8. The method of claim 7, wherein, once the metal coupon is inserted in the CIVC, sub-step ii further comprises hermetically sealing the CIVC containing the metal coupon, then, in vacuum pressure conditions, pouring the polymer or resin into the CIVC to its fullest capacity, and wherein the C2 valve or gate indicates when the CIVC is full.

9. The method of claim 1, wherein the polymer or resin is an acrylic, styrene, vinyl, or epoxy.

10. The method of claim 6, wherein sub-step ii finishes when the polymer or resin polymerizes.

11. The method of claim 7, wherein sub-step iii further comprises extracting the metal coupon and the polymer or resin from the CIVC through the lower cap, then washing, drying, weighing, and preparing the metal coupon for dissolution.

12. The method of claim 6, wherein sub step iv further comprises placing the metal coupon in a beaker, then flooding the metal coupon with concentrated hydrochloric acid (HCl).

13. The method of claim 7, wherein sub-step iv further comprises determining volume of the control chamber plus volume of the corrosion cavities through volume of remaining polymer or resin.

14. The method of claim 1, wherein step f) further comprises:
  i. Placing the polymer or resin replica in a Petri dish;
  ii. Dripping deionized water over the polymer or resin replica, avoiding damage to the polymer or resin replica; and
  iii. When the polymer or resin replica is fully washed, placing the polymer or resin replica in a desiccator for at least a day, and then obtaining a polymer or resin mold for determining the morphology of corrosion cavities.

15. The method of claim 1, wherein step g) further comprises fixing the polymer or resin replica, obtained in step f), to an aluminum stub by carbon double sided adhesive tape.

16. The method of claim 1, wherein step h) further comprises covering the polymer or resin replica of the morphology and topography of the corrosion cavities with carbon, gold, or gold/palladium.

17. The method of claim 1, wherein once the polymer or resin replica is coated with the thin film, step i) further comprises introducing the polymer or resin replica into an SEM vacuum chamber to determine:
  i) Shape of the corrosion cavities;
  ii) Maximum sizes of the corrosion cavities, by changing observation angles inside the SEM chamber;
  iii) Orientation of the corrosion cavities (Idem);
  iv) True length of the corrosion cavities; and
  v) Effective advance of corrosion.

18. The method of claim 1, wherein step j) further comprises calculating attacked metal volume through the following equation:

$$V_{CR} = V_{TR} - (V_1 + V_2 + V_{CA})$$

where:

$V_{CR}$ is attacked metal volume;

$V_{TR}$ is polymer or resin total volume;

$V_1$ and $V_2$ are known volumes of C1 and C2, respectively; and $V_{CA}$ is known volume inside the CIVC.

19. The method of claim 1, wherein the method further comprises using a graphic interface to access the metal coupon information data, volumetric calculation, and gravimetric calculation, before and after being exposed to the corrosive environment, and the micrographs.

20. The method of claim 1, wherein the graphic interface comprises six sections:
  a) A first section including the metal coupon initial data information, before being exposed to the corrosive environment;
  b) A second section including the metal coupon data information, after being exposed to the corrosive environment;
  c) A third section showing results of gravimetric and volumetric calculations before and after the metal coupon is exposed to the corrosive environment;
  d) A fourth section where, starting with a sampling process, a statistical distribution of depths of both uniform and pitting corrosion are determined using both the information from sections a) through c) and electronic and/or light microscopy characterization;
  e) A fifth section where a maximum depth of corrosion penetration and maximum corrosion rate are determined, according to NACE SP0777-2013 Item No. 21017 recommendation, through a sampling process and through using the information obtained in sections a) through d); and
  f) A sixth section that illustrates with micrographs corrosive attack on the metal coupon.

* * * * *